(12) United States Patent
Weiner et al.

(10) Patent No.: US 8,962,583 B2
(45) Date of Patent: Feb. 24, 2015

(54) TREATMENT OF INFLAMMATORY DISEASES USING MIR-124

(75) Inventors: Howard Weiner, Brookline, MA (US); Eugene Ponomarev, Cambridge, MA (US); Tatyana Veremeyko, Cambridge, MA (US); Anna M. Krichevsky, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 140 days.

(21) Appl. No.: 13/379,374

(22) PCT Filed: Jun. 25, 2010

(86) PCT No.: PCT/US2010/039974
§ 371 (c)(1),
(2), (4) Date: Mar. 14, 2012

(87) PCT Pub. No.: WO2010/151755
PCT Pub. Date: Dec. 29, 2010

(65) Prior Publication Data
US 2012/0202870 A1 Aug. 9, 2012

Related U.S. Application Data

(60) Provisional application No. 61/220,281, filed on Jun. 25, 2009.

(51) Int. Cl.
*A61K 31/7105* (2006.01)
*A61K 48/00* (2006.01)
*C12N 15/113* (2010.01)

(52) U.S. Cl.
USPC .......... 514/44; 435/6.1; 435/91.1; 435/91.31; 435/455; 536/23.1

(58) Field of Classification Search
USPC .................. 435/6, 91.1, 91.31, 455; 514/44; 536/23.1, 24.5
See application file for complete search history.

(56) References Cited

U.S. PATENT DOCUMENTS

| 8,071,562 | B2* | 12/2011 | Bader et al. ................. 514/44 A |
| 2007/0292878 | A1 | 12/2007 | Raymond |
| 2008/0171715 | A1 | 7/2008 | Brown et al. |
| 2009/0192111 | A1* | 7/2009 | Bader et al. ..................... 514/44 |
| 2011/0117567 | A1* | 5/2011 | Kawano et al. ................... 435/6 |

FOREIGN PATENT DOCUMENTS

| WO | 2008/079303 | 7/2008 |
| WO | 2008/153692 | 12/2008 |

OTHER PUBLICATIONS

Ding et al., "Regulating the regulators: mechanisms controlling the maturation of microRNAs," Trends Biotechnol., 27:27-36 (2009).
Zhang and Su, "Small but influential: the role of microRNAs on gene regulatory network and 3'UTR evolution," J. Genet. Genomics, 36:1-6 (2009).
Bi et al., "MicroRNAs: novel regulators during the immune response," Cell Physiol., 218:467-472 (2009).
Naguibneva et al., "An LNA-based loss-of-function assay for microRNAs," Biomed. Pharmacother., 60:633-638 (2006).
Zhang et al., "C/EBPalpha redirects androgen receptor signaling through a unique bimodal interaction," Oncogene, 29(5):723-738 (2010, Epub 2009).
Zhao et al., "Protein kinase Cdelta stimulates proteasome-dependent degradation of C/EBPalpha during apoptosis induction of leukemic cells," PLoS One, 4(8):e6552 (2009).
Dhawan et al., J. Biol. Chem., 284(5):3086-3095 (2009, Epub 2008). Erratum in: J. Biol. Chem. 284(12):8208 (2009).
Wilson et al., "Macrophages: promising targets for the treatment of atherosclerosis," Curr. Vasc. Pharmacol., 7(2):234-243 (2009).
Boillee and Cleveland, "Revisiting oxidative damage in ALS: microglia, Nox, and mutant SOD1," J. Clin. Invest., 118(2):474-478 (2008).
Kim and Lee, "Role of innate immunity in triggering and tuning of autoimmune diabetes," Current Molecular Medicine, 9:30-44 (2009).
Olefsky and Glass, "Macrophages, inflammation, and insulin resistance," Annu. Rev. Physiol., 72:219-246 (2010).
Ma and Pope, "The role of macrophages in rheumatoid arthritis," Current Pharmaceutical Design, 11:569-580 (2005).
International Search Report issued in PCT/US2010/039974 on Mar. 29, 2011.
Lim et al., "Microarray analysis shows that some microRNAs downregulate large numbers of target mRNAs," Nature 433:769-773 (2005).
Cheng et al., "miR-124 regulates adult neurogenesis in the subventricular zone stem cell niche," Nat. Neurosci., 12:399-408 (2009).
Yu et al., "MicroRNA miR-124 regulates neurite outgrowth during neuronal differentiation," Exp. Cell Res., 314:2618-2633 (2008).
Makeyev et al., "The MicroRNA miR-124 promotes neuronal differentiation by triggering brain-specific alternative pre-mRNA splicing," Mol. Cell, 27:435-448 (2007).
Landgraf et al., "A mammalian microRNA expression atlas based on small RNA library sequencing," Cell, 129:1401-1414 (2007).
Fukao et al., "An evolutionarily conserved mechanism for microRNA-223 expression revealed by microRNA gene profiling," Cell, 129:617-631 (2007).

(Continued)

*Primary Examiner* — Jane Zara
(74) *Attorney, Agent, or Firm* — Fish & Richardson P.C.

(57) ABSTRACT

Methods of treating, reducing the risk of developing, or delaying the onset of an inflammatory disease are disclosed. The methods involved providing a subject with or at risk of developing an inflammatory disease and administering to the subject an effective amount of a first therapeutic composition comprising miR-124. Further provided are methods of diagnosing a subject with or at risk of developing an inflammatory disease.

5 Claims, 24 Drawing Sheets

(56) References Cited

OTHER PUBLICATIONS

Smirnova et al., "Regulation of miRNA expression during neural cell specification," Eur. J. Neurosci., 21:1469-1477 (2005).

Kim et al., "Identification of many microRNAs that copurify with polyribosomes in mammalian neurons," Proc. Natl. Acad. Sci. USA, 101:360-365 (2004).

Zhang et al., "Enhancement of hematopoietic stem cell repopulating capacity and self-renewal in the absence of the transcription factor C/EBP alpha," Immunity, 21:853-863 (2004).

Feng et al., "PU.1 and C/EBPalpha/beta convert fibroblasts into macrophage-like cells," Proc. Natl. Acad. Sci. USA, 105:6057-6062 (2008).

Nakanishi et al., "Responses of microRNAs 124a and 223 following spinal cord injury in mice," Spinal Cord, 48(3):192-196 (2009).

Pierson et al., "Regulation of cyclin dependent kinase 6 by microRNA 124 in medulloblastoma,". J. Neurooncol., 90:1-7 (2008).

Silber et al., "miR-124 and miR-137 inhibit proliferation of glioblastoma multiforme cells and induce differentiation of brain tumor stem cells," BMC Med., 6:14 (2008).

Mishima et al., "RT-PCR-based analysis of microRNA (miR-1 and -124) expression in mouse CNS," Brain Res., 1131:37-43 (2007).

Visvanathan et al., "The microRNA miR-124 antagonizes the anti-neural REST/SCP1 pathway during embryonic CNS development," Genes Dev., 21:744-749 (2007).

\* cited by examiner

FIG. 1A
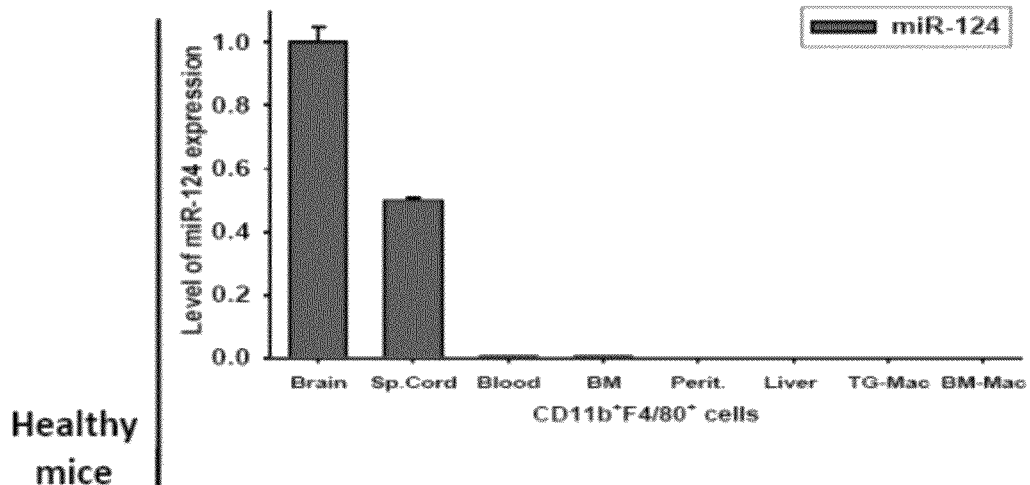
FIG. 1B
FIG. 1C
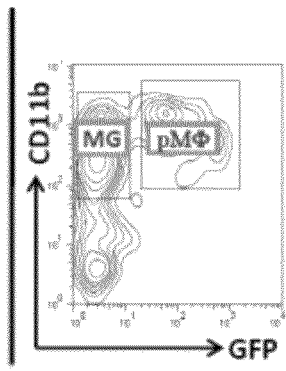
FIG. 1D
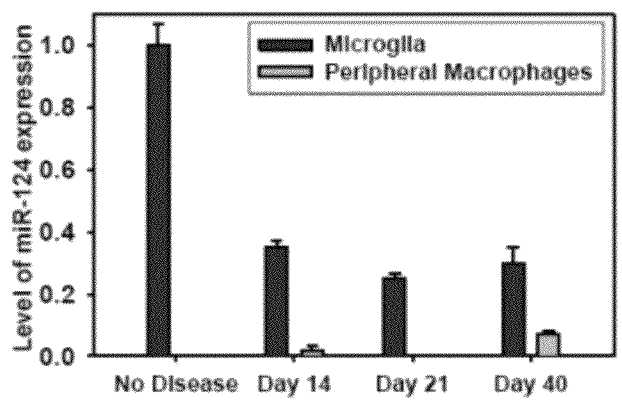

FIG. 1E
| | Threshold Cycle (Ct) | |
|---|---|---|
| | miR-124 | snoR-55 |
| Microglia | 25.0271 | 27.5366 |
| | 24.4766 | 26.7754 |
| | 24.4428 | 27.1563 |
| Neurons | 25.3551 | 27.8309 |
| | 25.1342 | 27.6783 |
| | 25.0969 | 27.7546 |
FIG. 1F
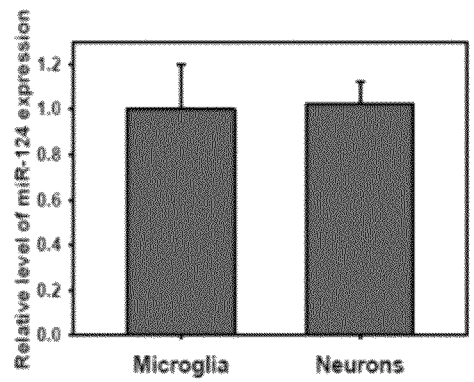
FIG. 1G
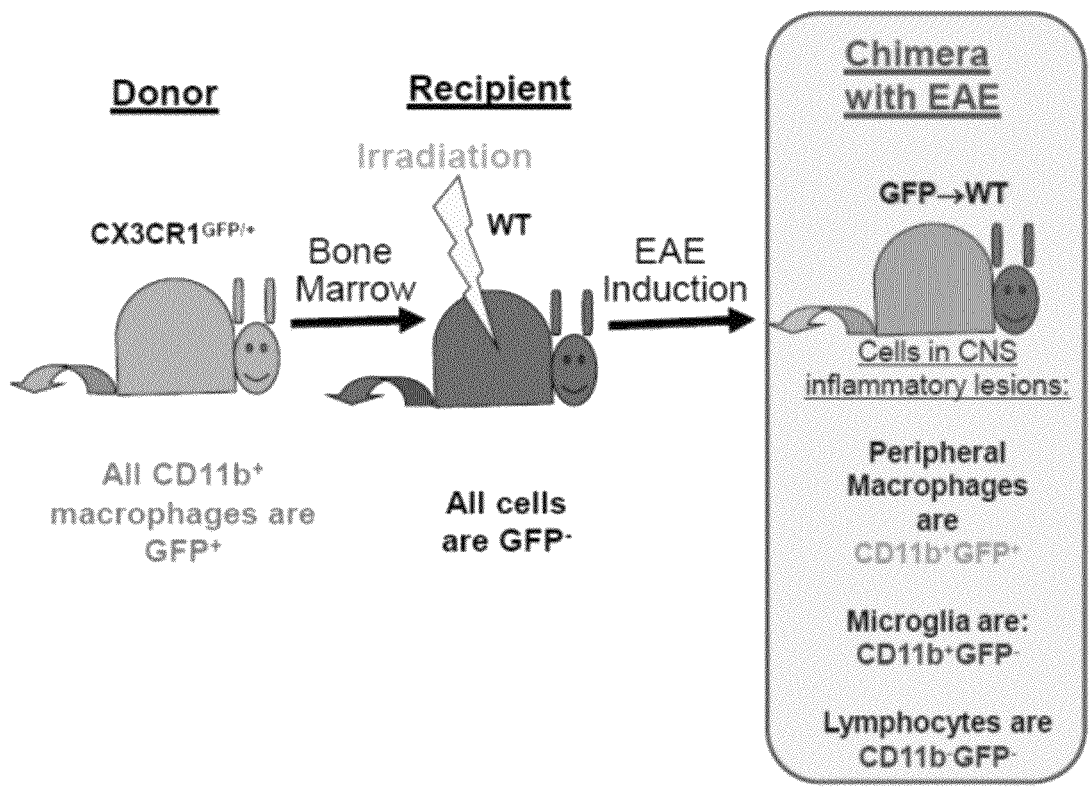

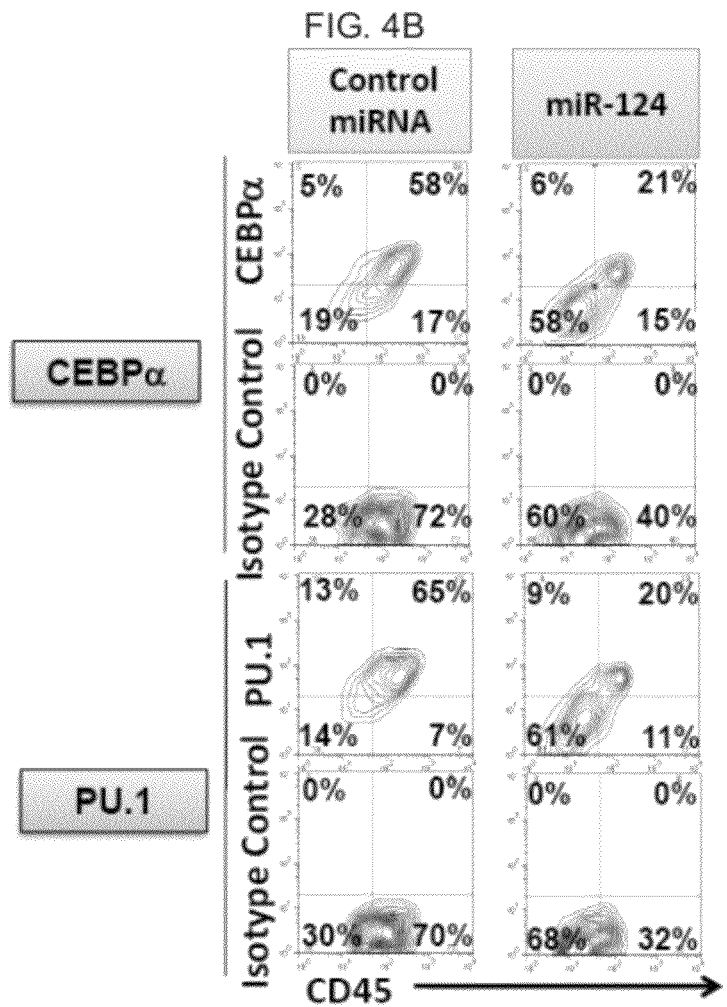
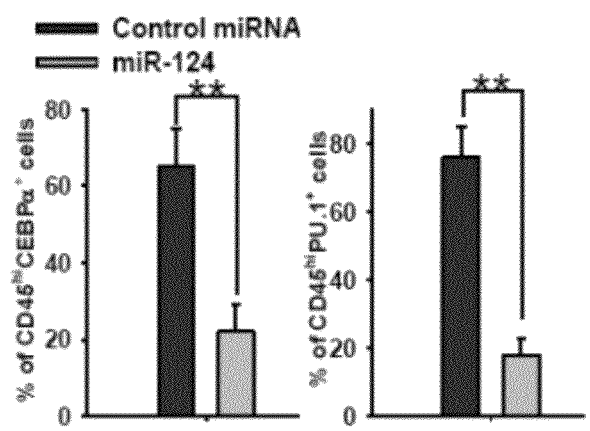

FIG. 4D

| | Site 1 | SEQ ID NO: |
|---|---|---|
| | CEBPA 3' UTR (nt 289-295) | |
| miR-124 3'-5' | CCGUAAGUGGCGCACGGAAU | 1 |
| | \|\| \| \| \|\|\| :\|\|\|\|\|\|\|: | |
| M. Musculus | aGGaAgUaACCuUGUGCCUUG | 24 |
| H. sapiens | aGGa--UaACCuUGUGCCUUG | 25 |
| P. troglodytes | aGGa--UaACCuUGUGCCUUG | 26 |
| M. mulatta | aGGa--UaACCuUGUGCCUUG | 27 |
| R. Norvegicus | aGGaAgUaACCuUGUGCCUUG | 28 |
| O. cuniculus | aGGag-UaACCGUGUGCCUUG | 29 |
| | Site 2 | |
| | CEBPA 3' UTR (nt 345-351) | |
| miR-124 3'-5' | CCGUAAGUGGCGCACGGAAU | 1 |
| | \|\| : \| :\|\|\|\|\|\|\|: | |
| M. Musculus | gGGaGcaaAa-aUGUGCCUUG | 30 |
| H. sapiens | gGGaGcaaAU--CGUGCCUUG | 31 |
| P. troglodytes | gGGaGcaaAU--CGUGCCUUG | 32 |
| M. mulatta | gGGaGcaaAU--CGUGCCUUG | 33 |
| R. Norvegicus | gGGaGcaaAC-aUGUGCCUUG | 34 |
| O. cuniculus | gGGaGcaaAU-aCGUGCCUUG | 35 |
| | Site 3 | |
| | CEBPA 3' UTR (nt 938-944) | |
| miR-124 3'-5' | CCGUAAGUGGCGCACGGAAU | 1 |
| | \| \| \|\|\|\|\|\|\|: | |
| M. Musculus | u--g-UcCcagcgGUGCCUUG | 36 |
| H. sapiens | u--g-ccCcagcaGUGCCUUG | 37 |
| P. troglodytes | u--g-ccCcagcaGUGCCUUG | 38 |
| M. mulatta | u--g-ccCcagcaGUGCCUUG | 39 |
| R. Norvegicus | u--g-UcCcagcgGUGCCUUG | 40 |
| O. cuniculus | uccg-UcCcggcgCUGCCUUG | 41 |

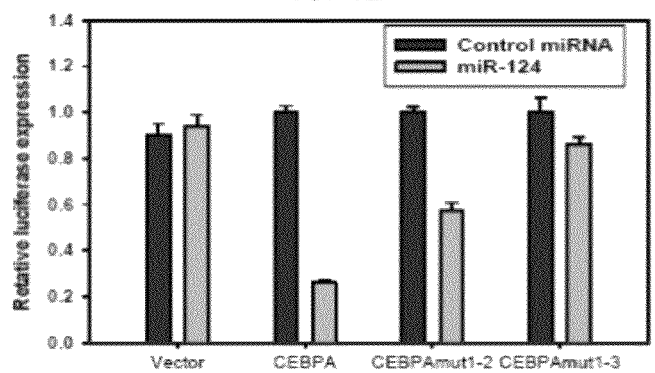
FIG. 4E
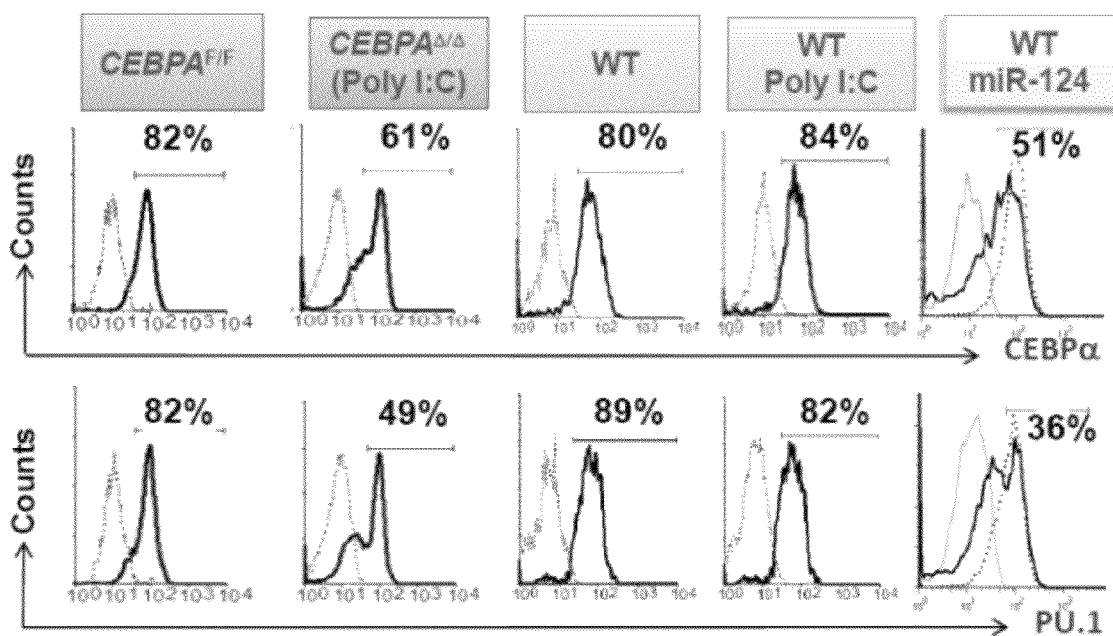
FIG. 4F
FIG. 4G

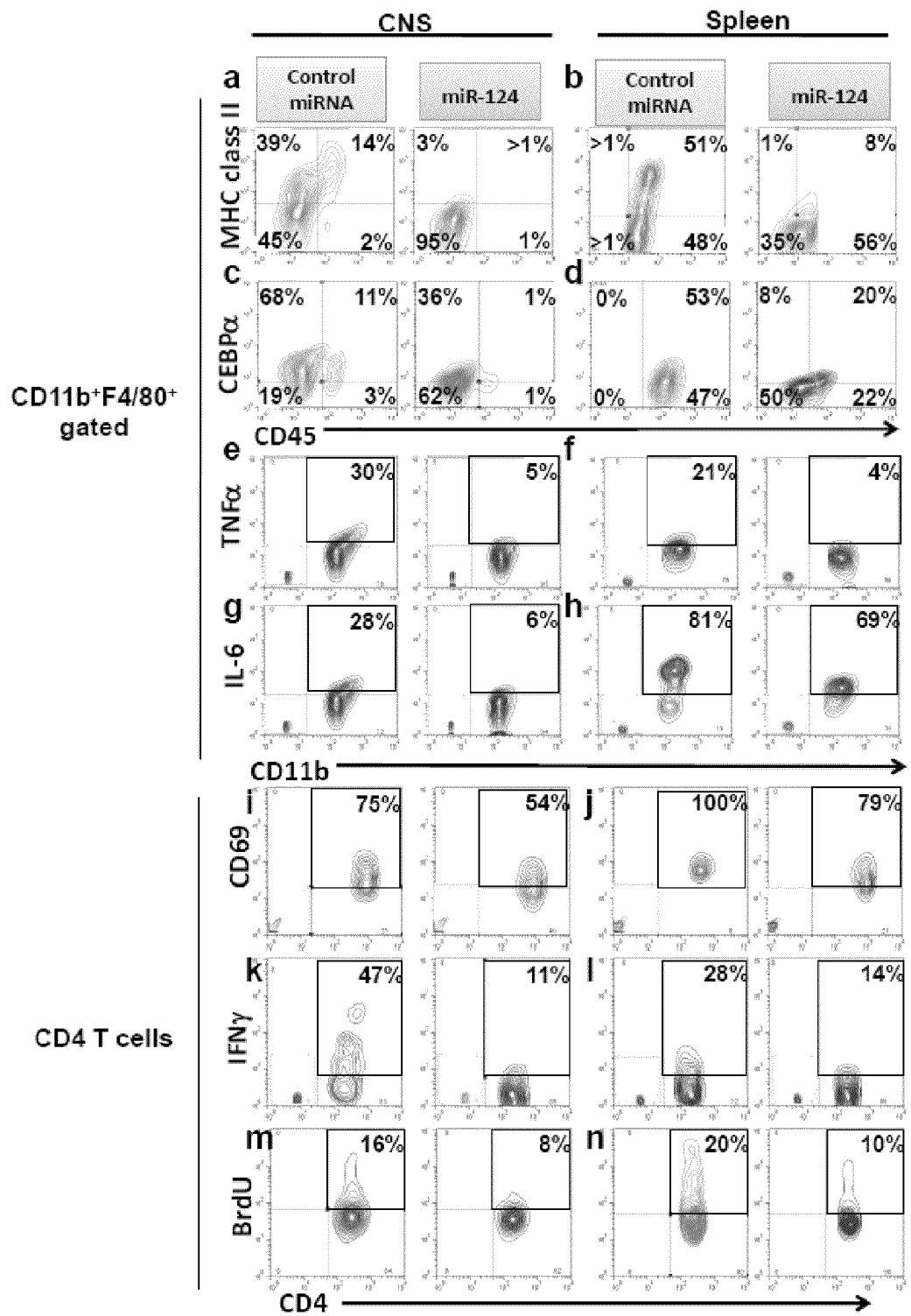
FIGs. 7A-N

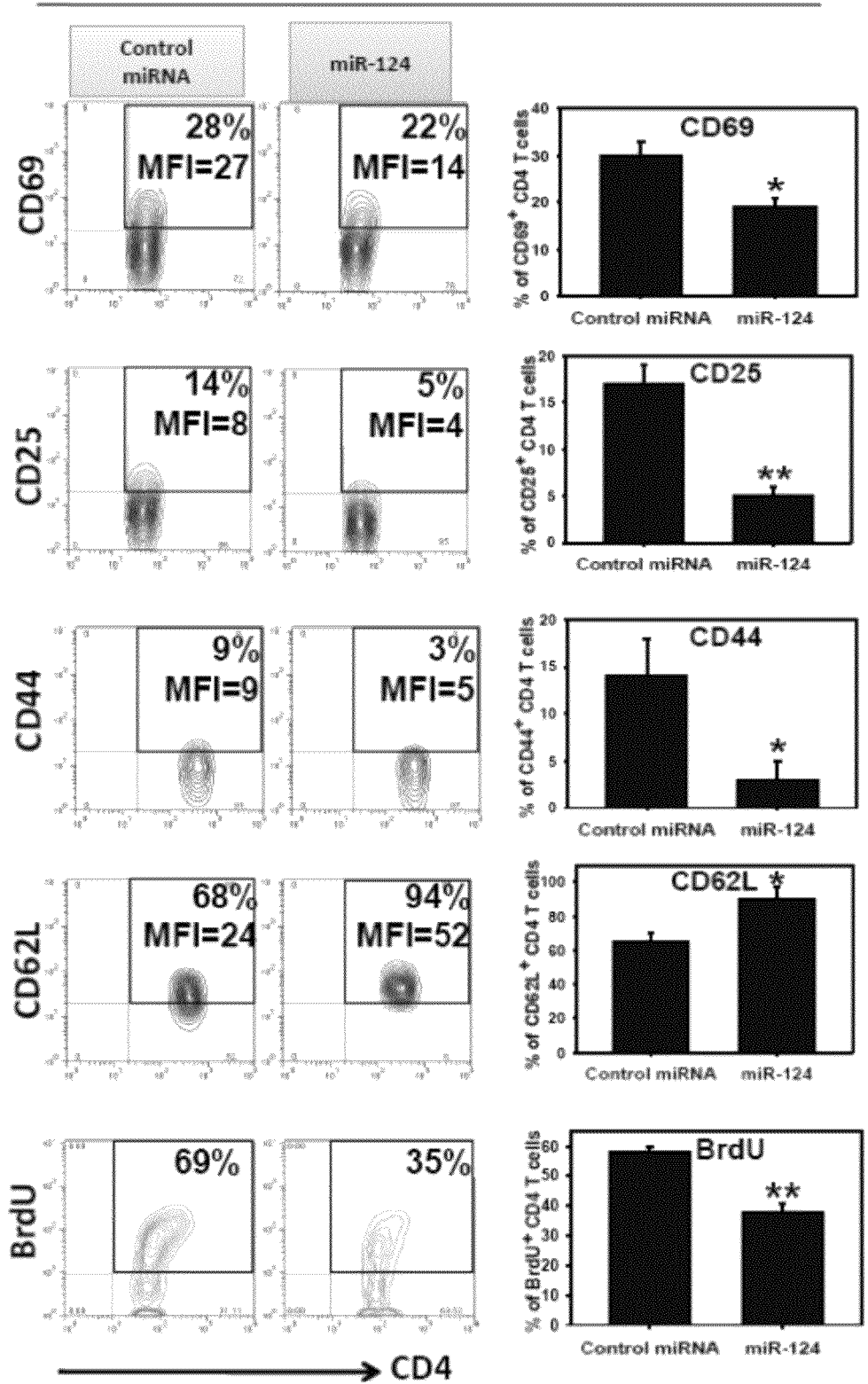

FIG. 8A
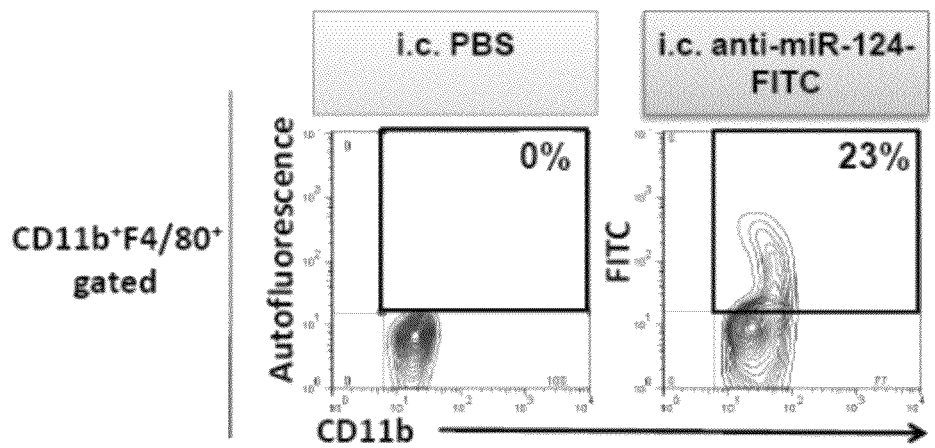
FIG. 8B
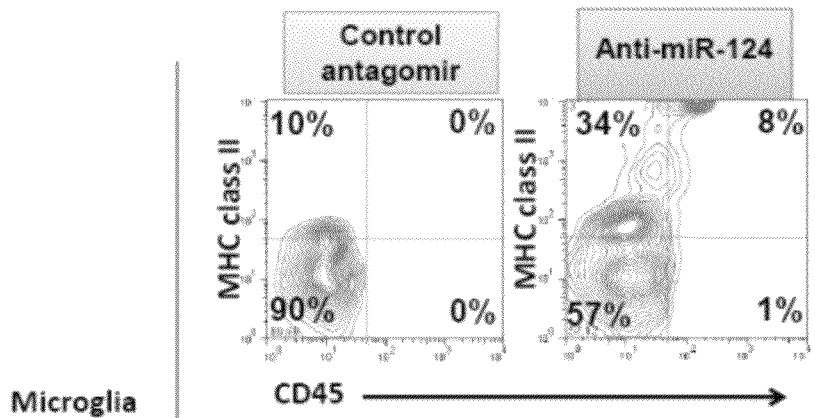
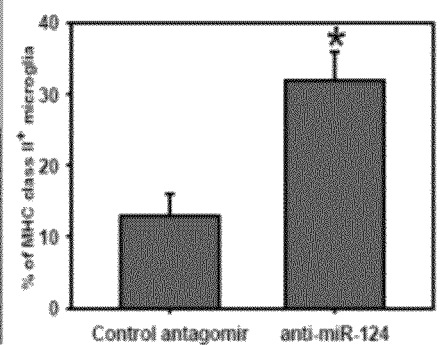
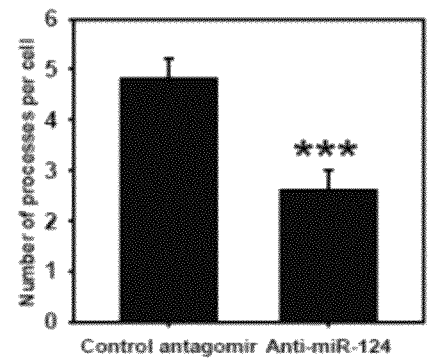
FIG. 8C
FIG. 8D

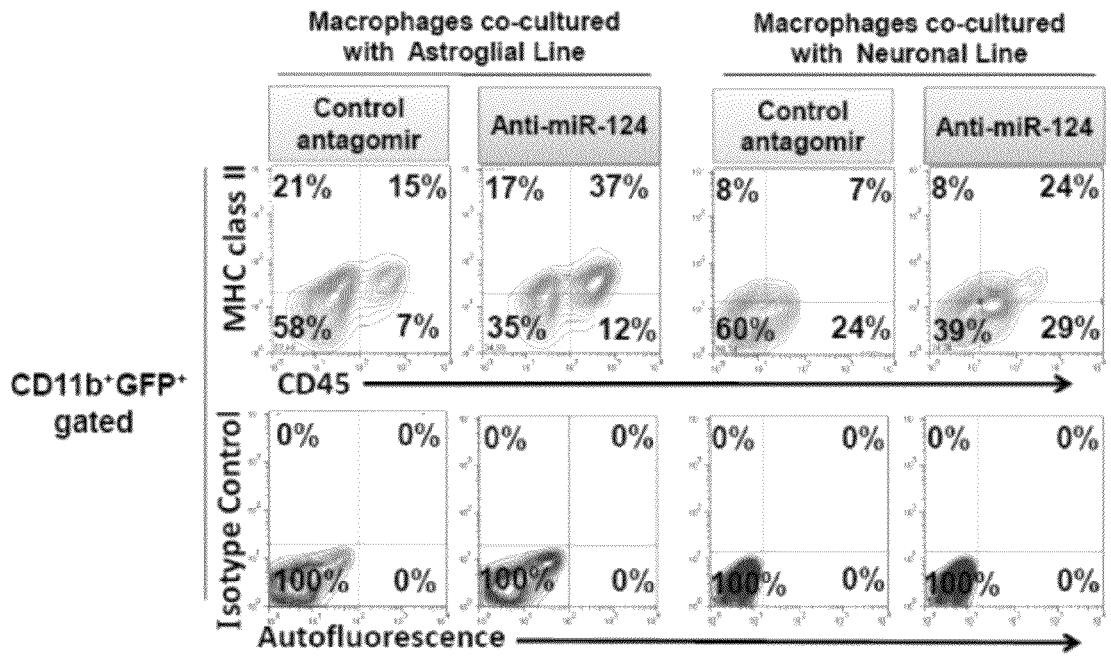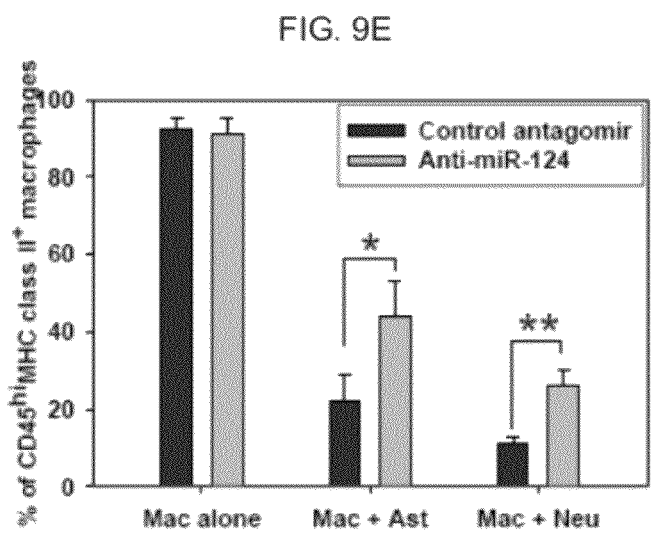

FIG. 11

Homo sapiens miR-124 stem loop sequences
Has-mir-124-1 (MI0000443)
AGGCCUCUCUCUCCGUGUUCACAGCGGACCUUGAUUUAAAUGUCCAUACAAUUAAGGCACGCGG
UGAAUGCCAAGAAUGGGGCUG   (SEQ ID NO:2)
hsa-mir-124-2 (MI0000444)
AUCAAGAUUAGAGGCUCUGCUCUCCGUGUUCACAGCGGACCUUGAUUUAAUGUCAUACAAUUAA
GGCACGCGGUGAAUGCCAAGAGCGGAGCCUACGGCUGCACUUGAA (SEQ ID NO:3)
hsa-mir-124-3 (MI0000445)
UGAGGGCCCCUCUGCGUGUUCACAGCGGACCUUGAUUUAAUGUCUAUACAAUUAAGGCACGCGG
UGAAUGCCAAGAGAGGCGCCUCC (SEQ ID NO:4)

Mus musculus miR-124 stem loop sequences
mmu-mir-124-1 (MI0000716)
AGGCCUCUCUCUCCGUGUUCACAGCGGACCUUGAUUUAAAUGUCCAUACAAUUAAGGCACGCGG
UGAAUGCCAAGAAUGGGGCUG (SEQ ID NO:5)
mmu-mir-124-2 (MI0000717)
AUCAAGAUCAGAGACUCUGCUCUCCGUGUUCACAGCGGACCUUGAUUUAAUGUCAUACAAUUAA
GGCACGCGGUGAAUGCCAAGAGCGGAGCCUACGGCUGCACUUGAA (SEQ ID NO:6)
Mmu-mir-124-3 (MI0000150)
CUCUGCGUGUUCACAGCGGACCUUGAUUUAAUGUCUAUACAAUUAAGGCACGCGGUGAAUGCCA
AGAG (SEQ ID NO:7)

Rattus norvegicus miR-124 stem loop sequences
rno-mir-124-1 stem loop (MI0000893)
AGGCCUCUCUCUCCGUGUUCACAGCGGACCUUGAUUUAAAUGUCCAUACAAUUAAGGCACGCGG
UGAAUGCCAAGAAUGGGGCUG (SEQ ID NO:8)
rno-mir-124-2 (MI0000894)
AUCAAGAUCAGAGACUCUGCUCUCCGUGUUCACAGCGGACCUUGAUUUAAUGUCAUACAAUUAA
GGCACGCGGUGAAUGCCAAGAGCGGAGCCUACGGCUGCACUUGAA (SEQ ID NO:9)
rno-mir-124-3 (MI0000892)
UGAGGGCCCCUCUGCGUGUUCACAGCGGACCUUGAUUUAAUGUCUAUACAAUUAAGGCACGCGG
UGAAUGCCAAGAGAGGCGCCUCC (SEQ ID NO:10)

Homo sapiens miR-506 stem loop sequence
hsa-mir-506 stem loop (MI0003193)
GCCACCACCAUCAGCCAUACUAUGUGUAGUGCCUUAUUCAGGAAGGUGUUACUUAAUAGAUUAA
UAUUUGUAAGGCACCCUUCUGAGUAGAGUAAUGUGCAACAUGGACAACAUUUGUGGUGGC
 (SEQ ID NO:11)

SEQUENCE LISTING

```
<160> NUMBER OF SEQ ID NOS: 41

<210> SEQ ID NO 1
<211> LENGTH: 20
<212> TYPE: RNA
<213> ORGANISM: Homo sapien

<400> SEQUENCE: 1
uaaggcacgc ggugaaugcc                                              20

<210> SEQ ID NO 2
<211> LENGTH: 85
<212> TYPE: RNA
<213> ORGANISM: Homo sapiens

<400> SEQUENCE: 2
aggccucucu cuccguguuc acagcggacc uugauuuaaa uguccauaca auuaaggcac    60
gcggugaaug ccaagaaugg ggcug                                         85
```

<210> SEQ ID NO 3
<211> LENGTH: 109
<212> TYPE: RNA
<213> ORGANISM: Homo sapiens

<400> SEQUENCE: 3
aucaagauua gaggcucugc ucuccguguu cacagcggac cuugauuuaa ugucauacaa    60
uuaaggcacg cggugaaugc caagagcgga gccuacggcu gcacuugaa               109

<210> SEQ ID NO 4
<211> LENGTH: 87
<212> TYPE: RNA
<213> ORGANISM: Homo sapiens

<400> SEQUENCE: 4
ugagggcccc ucugcguguu cacagcggac cuugauuuaa ugucuauaca auuaaggcac    60
gcggugaaug ccaagagagg cgccucc                                        87

<210> SEQ ID NO 5
<211> LENGTH: 85
<212> TYPE: RNA
<213> ORGANISM: Mus musculus

<400> SEQUENCE: 5
aggccucucu cuccguguuc acagcggacc uugauuuaaa uguccauaca auuaaggcac    60
gcggugaaug ccaagaaugg ggcug                                          85

<210> SEQ ID NO 6
<211> LENGTH: 109
<212> TYPE: RNA
<213> ORGANISM: Mus musculus

<400> SEQUENCE: 6
aucaagauca gagacucugc ucuccguguu cacagcggac cuugauuuaa ugucauacaa    60
uuaaggcacg cggugaaugc caagagcgga gccuacggcu gcacuugaa               109

<210> SEQ ID NO 7
<211> LENGTH: 68
<212> TYPE: RNA
<213> ORGANISM: Mus musculus

<400> SEQUENCE: 7
cucugcgugu ucacagcgga ccuugauuua augucuauac aauuaaggca cgcggugaau    60
gccaagag                                                             68

<210> SEQ ID NO 8
<211> LENGTH: 85
<212> TYPE: RNA
<213> ORGANISM: Rattus norvegicus

<400> SEQUENCE: 8
aggccucucu cuccguguuc acagcggacc uugauuuaaa uguccauaca auuaaggcac    60
gcggugaaug ccaagaaugg ggcug                                          85

<210> SEQ ID NO 9
<211> LENGTH: 109
<212> TYPE: RNA
<213> ORGANISM: Rattus norvegicus

<400> SEQUENCE: 9
aucaagauca gagacucugc ucuccguguu cacagcggac cuugauuuaa ugucauacaa    60
uuaaggcacg cggugaaugc caagagcgga gccuacggcu gcacuugaa               109

<210> SEQ ID NO 10
<211> LENGTH: 87
<212> TYPE: RNA
<213> ORGANISM: Rattus norvegicus

<400> SEQUENCE: 10
ugagggcccc ucugcguguu cacagcggac cuugauuuaa ugucuauaca auuaaggcac    60
gcggugaaug ccaagagagg cgccucc                                       87

<210> SEQ ID NO 11
<211> LENGTH: 124
<212> TYPE: RNA
<213> ORGANISM: Homo sapiens

<400> SEQUENCE: 11
gccaccacca ucagccauac uauguguagu gccuuauuca ggaagguguu acuuaauaga    60
uuaauauuug uaaggcaccc uucugaguag aguaaugugc aacauggaca acauuugugg   120
uggc                                                                124

<210> SEQ ID NO 12
<211> LENGTH: 20
<212> TYPE: DNA
<213> ORGANISM: Artificial Sequence
<220> FEATURE:
<223> OTHER INFORMATION: Synthetically generated oligonucleotides

<400> SEQUENCE: 12
cauucaccgc gtgccuuauu                                               20

<210> SEQ ID NO 13
<211> LENGTH: 21
<212> TYPE: DNA
<213> ORGANISM: Artificial Sequence
<220> FEATURE:
<223> OTHER INFORMATION: Synthetically generated oligonucleotides

<400> SEQUENCE: 13
aguacugcuu acgauacggt t                                             21

<210> SEQ ID NO 14
<211> LENGTH: 21
<212> TYPE: DNA
<213> ORGANISM: Artificial Sequence
<220> FEATURE:
<223> OTHER INFORMATION: Synthetically generated oligonucleotides

<400> SEQUENCE: 14
ccguaucgua agcaguacut t                                             21

<210> SEQ ID NO 15
<211> LENGTH: 20
<212> TYPE: RNA
<213> ORGANISM: Artificial Sequence
<220> FEATURE:
<223> OTHER INFORMATION: Synthetically generated oligonucleotides

<400> SEQUENCE: 15
uuuccgacgc ggugaauucc                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetically generated oligonucleotides

<400> SEQUENCE: 16
aauucaccgc gtcggaaauu                                              20

<210> SEQ ID NO 17
<211> LENGTH: 21
<212> TYPE: DNA
<213> ORGANISM: Artificial Sequence
<220> FEATURE:
<223> OTHER INFORMATION: Synthetically generated oligonucleotides

<400> SEQUENCE: 17
ccgcuccaau gccuacugat t                                            21

<210> SEQ ID NO 18
<211> LENGTH: 21
<212> TYPE: DNA
<213> ORGANISM: Artificial Sequence
<220> FEATURE:
<223> OTHER INFORMATION: Synthetically generated oligonucleotides

<400> SEQUENCE: 18
ucaguaggca uuggagcggt g                                            21

<210> SEQ ID NO 19
<211> LENGTH: 19
<212> TYPE: DNA
<213> ORGANISM: Artificial Sequence
<220> FEATURE:
<223> OTHER INFORMATION: Synthetically generated oligonucleotides

<400> SEQUENCE: 19
gaacagcaac gagtaccgg                                               19

<210> SEQ ID NO 20
<211> LENGTH: 19
<212> TYPE: DNA
<213> ORGANISM: Artificial Sequence
<220> FEATURE:
<223> OTHER INFORMATION: Synthetically generated oligonucleotides

<400> SEQUENCE: 20
ccttgtgcct tggaaatgc                                               19

<210> SEQ ID NO 21
<211> LENGTH: 19
<212> TYPE: DNA
<213> ORGANISM: Artificial Sequence
<220> FEATURE:
<223> OTHER INFORMATION: Synthetically generated oligonucleotides

<400> SEQUENCE: 21
cacttgtatc tggcctctg                                               19

<210> SEQ ID NO 22
<211> LENGTH: 21
<212> TYPE: RNA
<213> ORGANISM: Artificial Sequence
<220> FEATURE:
<223> OTHER INFORMATION: Synthetically generated oligonucleotides

```
<400> SEQUENCE: 22
gucggccagg aacucgucgu u                                              21

<210> SEQ ID NO 23
<211> LENGTH: 21
<212> TYPE: RNA
<213> ORGANISM: Artificial Sequence
<220> FEATURE:
<223> OTHER INFORMATION: Synthetically generated oligonucleotides

<400> SEQUENCE: 23
cgacgaguuc cuggccgacu u                                              21

<210> SEQ ID NO 24
<211> LENGTH: 21
<212> TYPE: RNA
<213> ORGANISM: Artificial Sequence
<220> FEATURE:
<223> OTHER INFORMATION: Synthetically generated oligonucleotides

<400> SEQUENCE: 24
aggaaguaac cuugugccuu g                                              21

<210> SEQ ID NO 25
<211> LENGTH: 19
<212> TYPE: RNA
<213> ORGANISM: Artificial Sequence
<220> FEATURE:
<223> OTHER INFORMATION: Synthetically generated oligonucleotides

<400> SEQUENCE: 25
aggauaaccu ugugccuug                                                 19

<210> SEQ ID NO 26
<211> LENGTH: 19
<212> TYPE: RNA
<213> ORGANISM: Artificial Sequence
<220> FEATURE:
<223> OTHER INFORMATION: Synthetically generated oligonucleotides

<400> SEQUENCE: 26
aggauaaccu ugugccuug                                                 19

<210> SEQ ID NO 27
<211> LENGTH: 19
<212> TYPE: RNA
<213> ORGANISM: Artificial Sequence
<220> FEATURE:
<223> OTHER INFORMATION: Synthetically generated oligonucleotides

<400> SEQUENCE: 27
aggauaaccu ugugccuug                                                 19

<210> SEQ ID NO 28
<211> LENGTH: 21
<212> TYPE: RNA
<213> ORGANISM: Artificial Sequence
<220> FEATURE:
<223> OTHER INFORMATION: Synthetically generated oligonucleotides

<400> SEQUENCE: 28
aggaaguaac cuugugccuu g                                              21

<210> SEQ ID NO 29
```

```
<210> SEQ ID NO 29
<211> LENGTH: 20
<212> TYPE: RNA
<213> ORGANISM: Artificial Sequence
<220> FEATURE:
<223> OTHER INFORMATION: Synthetically generated oligonucleotides

<400> SEQUENCE: 29
aggaguaacc gugugccuug                                                   20

<210> SEQ ID NO 30
<211> LENGTH: 20
<212> TYPE: RNA
<213> ORGANISM: Artificial Sequence
<220> FEATURE:
<223> OTHER INFORMATION: Synthetically generated oligonucleotides

<400> SEQUENCE: 30
gggagcaaaa augugccuug                                                   20

<210> SEQ ID NO 31
<211> LENGTH: 19
<212> TYPE: RNA
<213> ORGANISM: Artificial Sequence
<220> FEATURE:
<223> OTHER INFORMATION: Synthetically generated oligonucleotides

<400> SEQUENCE: 31
gggagcaaau cgugccuug                                                    19

<210> SEQ ID NO 32
<211> LENGTH: 19
<212> TYPE: RNA
<213> ORGANISM: Artificial Sequence
<220> FEATURE:
<223> OTHER INFORMATION: Synthetically generated oligonucleotides

<400> SEQUENCE: 32
gggagcaaau cgugccuug                                                    19

<210> SEQ ID NO 33
<211> LENGTH: 19
<212> TYPE: RNA
<213> ORGANISM: Artificial Sequence
<220> FEATURE:
<223> OTHER INFORMATION: Synthetically generated oligonucleotides

<400> SEQUENCE: 33
gggagcaaau cgugccuug                                                    19

<210> SEQ ID NO 34
<211> LENGTH: 20
<212> TYPE: RNA
<213> ORGANISM: Artificial Sequence
<220> FEATURE:
<223> OTHER INFORMATION: Synthetically generated oligonucleotides

<400> SEQUENCE: 34
gggagcaaac augugccuug                                                   20

<210> SEQ ID NO 35
<211> LENGTH: 20
<212> TYPE: RNA
<213> ORGANISM: Artificial Sequence
<220> FEATURE:
<223> OTHER INFORMATION: Synthetically generated oligonucleotides

<400> SEQUENCE: 35
```
gggagcaaau acgugccuug                                                      20

<210> SEQ ID NO 36
<211> LENGTH: 18
<212> TYPE: RNA
<213> ORGANISM: Artificial Sequence
<220> FEATURE:
<223> OTHER INFORMATION: Synthetically generated oligonucleotides

<400> SEQUENCE: 36
ugucccagcg gugccuug                                                        18

<210> SEQ ID NO 37
<211> LENGTH: 18
<212> TYPE: RNA
<213> ORGANISM: Artificial Sequence
<220> FEATURE:
<223> OTHER INFORMATION: Synthetically generated oligonucleotides

<400> SEQUENCE: 37
ugccccagca gugccuug                                                        18

<210> SEQ ID NO 38
<211> LENGTH: 18
<212> TYPE: RNA
<213> ORGANISM: Artificial Sequence
<220> FEATURE:
<223> OTHER INFORMATION: Synthetically generated oligonucleotides

<400> SEQUENCE: 38
ugccccagca gugccuug                                                        18

<210> SEQ ID NO 39
<211> LENGTH: 18
<212> TYPE: RNA
<213> ORGANISM: Artificial Sequence
<220> FEATURE:
<223> OTHER INFORMATION: Synthetically generated oligonucleotides

<400> SEQUENCE: 39
ugccccagca gugccuug                                                        18

<210> SEQ ID NO 40
<211> LENGTH: 18
<212> TYPE: RNA
<213> ORGANISM: Artificial Sequence
<220> FEATURE:
<223> OTHER INFORMATION: Synthetically generated oligonucleotides

<400> SEQUENCE: 40
ugucccagcg gugccuug                                                        18

<210> SEQ ID NO 41
<211> LENGTH: 20
<212> TYPE: RNA
<213> ORGANISM: Artificial Sequence
<220> FEATURE:
<223> OTHER INFORMATION: Synthetically generated oligonucleotides

<400> SEQUENCE: 41
uccgucccgg cgcugccuug                                                      20

US 8,962,583 B2

TREATMENT OF INFLAMMATORY DISEASES USING MIR-124

CLAIM OF PRIORITY

This application is a 371 application of International Application No. PCT/US2010/039974, filed on Jun. 25, 2010, and claims the benefit of U.S. Patent Application Ser. No. 61/220,281, filed on Jun. 25, 20102009, the entire contents of which are hereby incorporated by reference.

FEDERALLY SPONSORED RESEARCH OR DEVELOPMENT

This invention was made with Government support under Grant No. R01 AG027437 awarded by the National Institutes of Health. The Government has certain rights in the invention.

BACKGROUND

Multiple sclerosis (MS) is an inflammatory disease characterized by multiple foci of inflammation and infiltration of macrophages and encephalitogenic T cells in the central nervous system. There are two types of macrophages found within the CNS of MS patients: resident macrophages or microglia, which are also present in normal CNS, and inflammatory macrophages the migrate into the CNS from the periphery. Microglia have a resting non-activated phenotype, a very limited ability to stimulate encephalitogenic T cells, and are believed to play immunoregulatory and neuroprotective roles. Peripheral macrophages appear in the CNS during inflammation and these cells have a highly activated phenotype, efficiently stimulate expansion of encephalitogenic T cells, and are thought to contribute to neuronal tissue destruction.

SUMMARY

The present disclosure is based, at least in part, on the discovery that microRNA 124 (miR-124) (5'-UAAG-GCACGCGGUGAAUGCC-3' (SEQ ID NO:1)) is expressed in microglia but not in peripheral macrophages isolated from mice with experimental autoimmune encephalomyelitis (EAE), which is a mouse model of multiple sclerosis (MS). As described herein, miR-124 was found to be expressed in normal CNS-resident macrophages, but not inflammatory macrophages or normal macrophages isolated from blood, spleen, bone marrow, peritoneal cavity, or the liver. Further, overexpression of miR-124 deactivated inflammatory macrophages and converted them into microglia-like cells. miR-124 is believed to inhibit macrophage activation by targeting CEBPα, a transcription factor responsible for the differentiation of myeloid lineage cells. Intravenous injection of liposomes containing miR-124 markedly suppresses clinical EAE symptoms and inhibited the infiltration of encephalitogenic T cells and inflammatory macrophages into the CNS. Thus, provided are novel methods of treating, reducing the risk of developing, or delaying the onset of central nervous system (CNS) inflammatory diseases. Also provided are novel methods of identifying a subject with or at risk of developing a CNS inflammatory disease.

Provided herein is the use of micro RNA-124 (miR-124) or a precursor thereof comprising the sequence UAAG-GCACGCGGUGAAUGCC (SEQ ID NO:1) in the treatment of an inflammatory condition. Also provided are methods of treating an inflammatory condition using micro RNA-124 (miR-124) or a precursor thereof comprising the sequence UAAGGCACGCGGUGAAUGCC (SEQ ID NO:1). The methods can also be used to prevent (i.e., reduce the risk of) or delay development of the inflammatory condition.

In some embodiments, the inflammatory condition is a central nervous system (CNS) inflammatory disease, e.g., selected from the group consisting of Multiple Sclerosis, Experimental Autoimmune Encephalomyelitis, Alzheimer's, amyotrophic lateral sclerosis (ALS), and Parkinson's. In some embodiments, the inflammatory condition is an autoimmune disease, e.g., rheumatoid arthritis or type I diabetes. In some embodiments, the inflammatory condition is type II diabetes or atherosclerosis. In some embodiments, the disease is characterized by activation (e.g., hyperactivation) of macrophages.

In some embodiments, the miR-124 is formulated for systemic (e.g., oral or intravenous) administration.

Also provide herein are pharmaceutical composition comprising miR-124 or a precursor thereof comprising the sequence UAAGGCACGCGGUGAAUGCC (SEQ ID NO:1) and a suitable carrier. In some embodiments, the composition is suitable for systemic administration (e.g., oral or intravenous).

In some embodiments, the miR-124 or precursor thereof is modified. For example, the miR-124 or precursor thereof can be modified to include a cholesterol group, 2'-O-methyl group, a 2'-fluoro group, a 2'-O-methoxyethyl group, a phosphorothiate group, a boranophosphate group, or a 4'-thioribose group.

Provided herein are methods of treating, reducing the risk of developing, or delaying the onset of a CNS inflammatory disease in a subject. The methods comprise providing a subject with or at risk of developing a CNS inflammatory disease; and administering to the subject an effective amount of a first therapeutic composition comprising miR-124 or a precursor thereof. The composition can be administered locally or systemically. CNS inflammatory disease that can be treated in this manner include multiple sclerosis, experimental autoimmune encephalomyelitis, Alzheimer's disease, amyotrophic lateral sclerosis (ALS) and Parkinson's disease.

Also provided herein are methods of treating, reducing the risk of developing, or delaying the onset of a autoimmune disease in a subject. The methods comprise providing a subject with or at risk of developing an autoimmune disease; and administering to the subject an effective amount of a first therapeutic composition comprising miR-124 or a precursor thereof. The composition can be administered locally or systemically. Autoimmune diseases that can be treated in this manner include rheumatoid arthritis and type I diabetes.

Also provided herein are compositions comprising miR-124 or a precursor thereof and a suitable carrier. The compositions provided are suitable for local or systemic administration.

Also provided is miR-124 or a precursor thereof for use as a medicament. Additionally provided is the use of miR-124 or a precursor thereof for the manufacture of a medicament for the treating, reducing the risk of developing, or delaying the onset of a CNS inflammatory disease.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are

DESCRIPTION OF DRAWINGS

FIGS. 1a-b are bar graphs showing that MiR-124 is expressed in CNS-resident microglia but not in peripheral macrophages. Mononuclear cells were isolated from different tissues of healthy adult B6 mice, F4/80$^+$CD11b$^+$ cells were sorted, and miR-124 (a) and miR-223(b) expression was analyzed by real-time RT-PCR. Mean±S.D. of triplicate is shown. The data are representative of three independent experiments.

FIGS. 1c-d show the results of cell sorting experiments and miR-124 expression levels in chimeric mice that were prepared by transplanting bone marrow from CX3CR1$^{+/GFP}$ mice into lethally irradiated recipients; after eight weeks of reconstitution EAE was induced. Mononuclear cells from healthy chimeric mice (no disease) or chimeras with EAE were isolated at the onset (d14), peak of disease (d21) and recovery phase (d40), and the cells were stained for macrophage markers CD11b and F4/80. Fluorescence for GFP (x-axis) and staining for CD11b (y-axis) is shown for peak of disease in (c). Populations of F4/80$^+$CD11b$^+$GFP$^-$ microglia (c, left square gate) and F4/80$^+$CD11b$^+$GFP$^+$ peripheral macrophages (c, right square gate) were sorted at indicated time points, RNA was isolated, and miR-124 expression was assessed by real-time RT-PCR; a representative experiment of four is shown in (d).

FIGS. 1e-f show the results of quantitative real-time RT-PCR for miR-124a in adult microglia and cultured cortical neurons. The actual threshold cycle (Ct) data for miR-124 and housekeeping snoR-55 is shown in table format in 1e and relative miR-124a expression levels normalized to snoR-55 are shown in bar graph form in 1f.

FIG. 1g is a schematic illustration of the generation of bone marrow chimeras that allow microglia to be distinguished from peripheral macrophages in the CNS of mice with EAE. Lethally irradiated (950 Rad) B6 mice were transplanted with bone marrow from CX3CR1GFP/+ mice in which one allele of CX3CR1 gene has been replaced by the GFP gene. Since CX3CR1 is expressed in myeloid cells, all macrophages in CX3CR1GFP/+ are GFP-positive. Since radiation-resistant microglia have very slow turnover in adult CNS, 97-99% of all CD45lowCD11b+ cells were GFP-negative from 8 until 10-12 weeks after reconstitution. In our experiments, EAE was induced 8 weeks after reconstitution. In chimeric mice with EAE, mononuclear cells stained for macrophage marker CD11b could be easily subdivided into three distinct subsets: 1) CD11b+GFP− microglia; 2) CD11b+GFP+ peripheral macrophages; 3) CD11b-GFP-lymphocytes.

FIG. 4b is a set of eight FACS plots showing the expressions of CEBPα and CD45, or PU.1 and CD45 analyzed in BM-MΦ transfected twice with miR-124 or control miRNA using two-color flow cytometry. Population of miR-124-transfected CD45$^{low}$ cells were negative for CEBPα and PU.1 expression, as shown in double staining for cell-surface CD45 and intracellular CEBPα or PU.1 (lower left quadrants) Staining for CD45 (x-axes) and either CEBPa, PU.1 or corresponding isotype controls (y-axes) are shown.

FIG. 4c is a bar graph showing the mean±S.E. of percentage of CD45$^{hi}$CEBPα$^+$ and CD45$^{hi}$PU.1$^+$ cells calculated for four independent experiments. Two asterisks (**) indicate that decreases in percentages of CD45$^{hi}$CEBPα$^+$ and CD45$^{hi}$PU.1$^+$ populations are statistically significant ($p<0.01$).

FIG. 4d shows the alignment of three predicted miR-124 binding sites to CEBPα 3'UTR for different species FIG. 4e is a bar graph showing the results of experiments in which the target CEBPα mRNA was validated using a luciferase reporter construct with intact CEBPα 3'UTR and the similar reporter but mutated in either two or three miR-124 binding sites in the 3'-UTR. The NI-E115 cell line was transfected with the indicated constructs and either miR-124 or control miRNA; normalized levels of luciferase activity are shown.

FIGS. 4f-j are histograms (4f-g) and FACS plots (4h-j) showing that conditional knockout of the cebpa gene results in the reduced expression of CEBPa and PU.1 proteins and downregulation of activation markers CD11b, CD45, MHC class II, and CD86. Bone marrow-derived macrophages from B6 wild type (WT) or CEBPAF/F mice were expanded for five days with M-CSF as described in Methods, after which 100 ug/ml of Polyinosinic:polycytidylic acid (Poly I:C) (Sigma) was added to the cultures, and the cells were further incubated for 4 days to induce expression of Mx1-Cre and delete the cebpa gene (CEBPA$^{Δ/Δ}$ mice). Then the cells were stained and analyzed for intracellular CEBPa (4f), PU.1 (4g) and surface CD11b (4h), MHC class II (4i), CD86 (4j), and CD45 (4h-j). In (4f) and (4g), solid-line plots indicate the staining for CEBPa or PU.1 and the dotted-line plots indicate the staining obtained with appropriate isotype control antibodies. Transfection with miR-124 resulted it similar levels of downregulation of CEBPa (f,WT miR-124) and PU.1 (g, WT miR-124) when compared to conditional knockout. (f and g, CEBPA$^{Δ/Δ}$ Poly I:C:Grey line on the left shows staining for appropriate isotype control antibodies. Dotted line on the right shows staining of cells transfected with control miRNA.

FIGS. 7a-n are each pairs of FACS plots showing that peripheral administration of miR-124 results in deactivation of macrophages in the CNS and spleen, and reduced activation of CD4 T cells. Mice were injected i.v. with miR-124 or control miRNA on days 13, 16, 18, and 20 after EAE induction as for FIG. 6b, mononuclear cells were isolated from CNS (7a,c,e,g,i,k,m) and spleens (7b,d,f,h,j,l,n) on day 21 and stained for surface markers and intracellular expression of CEBPα (7c,d), TNFα (7e,f), IL-6 (7g,h), IFNγ (7k,l) and for BrdU incorporation (7m,n). BrdU was injected i.p. 14 hours prior to isolation of mononuclear cells. (7a-d) The cells were stained for CD11b, F4/80, CD45, and MHC class II (7a,b) or CEBPα (7c,d) and analyzed by four-color flow cytometry. Staining for CD45 (x-axis) and MHC class II or CEBPα (y-axis) of CD11b$^+$F4/80$^+$ gated cells is shown. (7e-h) The cells were stained for CD11b, F4/80 and either TNFα or IL-6. Staining for CD11b (x-axis) and either TNFα (y-axis) or IL-6 (y-axis) of CD11b$^+$F4/80$^+$ gated cells are shown. (7i-n) The cells were stained for CD3, CD4 and either CD69, or IFNγ, or BrdU. Staining for CD4 (x-axis) and either CD69 (y-axis), or IFNγ (y-axis), or BrdU (y-axis) of CD3$^+$CD4$^+$ gated cells is shown.

FIG. 7p is a set of 10 FACS plots and accompanying bar graphs showing that peripheral administration of miR-124 affects priming of MOG-specific T cells by decreasing their activation marker expression and proliferation. MOG TCR tg 2D2 mice were immunized with MOG peptide and injected i.v. with miR-124 or control miRNA on days 0, 2, 4, and 6. On day 7, splenocytes were isolated and double stained for CD4 and either CD69, or CD25, or CD44 or CD62L. CD4+ gated cells were analyzed for the expression of CD4 (x-axes), and either CD69, or CD25, or CD44, or CD62L (y-axes). The percentage of positive cells and mean fluorescence intensities (MFI) are shown. Representative contour plots and mean percentage±S.E. of five individual animals are shown. (*, p<0.05; , p<0.01). For the proliferation assay (lower panels), CD4 T cells were isolated using magnetic beads by negative selection and cultured with irradiated splenocytes for 48 hours in the presence of MOG peptide. BrdU was added 16 hrs prior to analysis. The cells were stained for CD4 (x-axis) and BrdU (y-axes), and the percentage of BrdU-positive CD4+ gated cells is shown in the two lower contour-plots. (, p<0.01).

FIGS. 8a-d show that a miR-124 inhibitor alters the quiescent phenotype of microglia in vivo. (8a) FITC-labeled anti-miR-124 or saline were injected intracranially into B6 mice and 24 hours later CNS mononuclear cells were stained with anti-CD11b antibody and analyzed for the expression of CD11b (x-axis) and FITC fluorescence (y-axis) by flow cytometry. (8b) Anti-miR-124 or a control antagomir were injected intracranially into B6→CX3CR1$^{GFP/-}$ chimeric mice and after three days CD11$^+$GFP$^+$ microglia was analyzed for the expression of CD45 (x-axis) and MHC class II (y-axis) by flow cytometry. (8c) Mean±S.E. of the percentage of MHC class II$^+$ microglia for four mice per group injected i.c. with either anti-miR-124 or control antagomir is shown. The number of processes for GFP$^+$ microglia was counted for at least one hundred cells using sections from 3-4 mice and the average number of processes per cell is shown in (8d). Three asterisks (***) indicate that decrease in the number of microglial processes in mice injected i.c. the miR-124 inhibitor is statistically significant (p<0.001)

FIGS. 9a-e show that miR-124 inhibitor reverses the microglia-like phenotype of macrophages co-cultured with neural and astroglial cells in vitro. BM-MΦ were isolated from ACTB-GFP Tg mice that ubiquitously express GFP under the actin promoter as described in Methods. The cells were either cultured alone or co-cultured with an astroglial (astrocyte type IC8-D1A) or neuronal (neuroblastoma NIE115) cell line for six days in media (9a,b) or in the presence of anti-miR-124 or a control antagomir (9c,d). The cells were then analyzed for the expression of GFP, CD11b, MHC class II and CD45 using four-color flow cytometry. (9a) CD11b$^+$GFP$^+$ gated macrophages cultured alone (left contour plot) or co-cultured with an astroglial (middle contour-plot) or neuronal (right contour-plot) cell line were analyzed for the expression of CD45 (x-axis) and MHC class II (y-axis). (9b) Expression of miR-124 was assessed by real-time RT-PCR in microglia, astroglial and neuronal lines, BM-MΦ cultured alone or in CD11b$^+$GFP$^+$ macrophages sorted from the co-cultures. (9c-e) Macrophages were cocultured with either an astroglial (9c) or neuronal (9d) cell line in the presence of anti-miR-124 or a control antagomir. CD11b$^+$GFP$^+$ gated cells were analyzed for expression of CD45 (x-axis) and MHC class II (y-axis). The data for three independent experiments are summarized in (9e) with mean±S.E. of the percentage of CD45$^{hi}$MHC class II$^-$ macrophages shown. One or two asterisks indicate that increases in percentage of CD45$^{hi}$MHC class II$^+$ are statistically significant (*, p<0.05; **, p<0.01).

FIG. 11 sets forth stem-loop sequences for human, mouse, and rat pre-miR-124 and for human pre-miR-506.

Figure 2A:
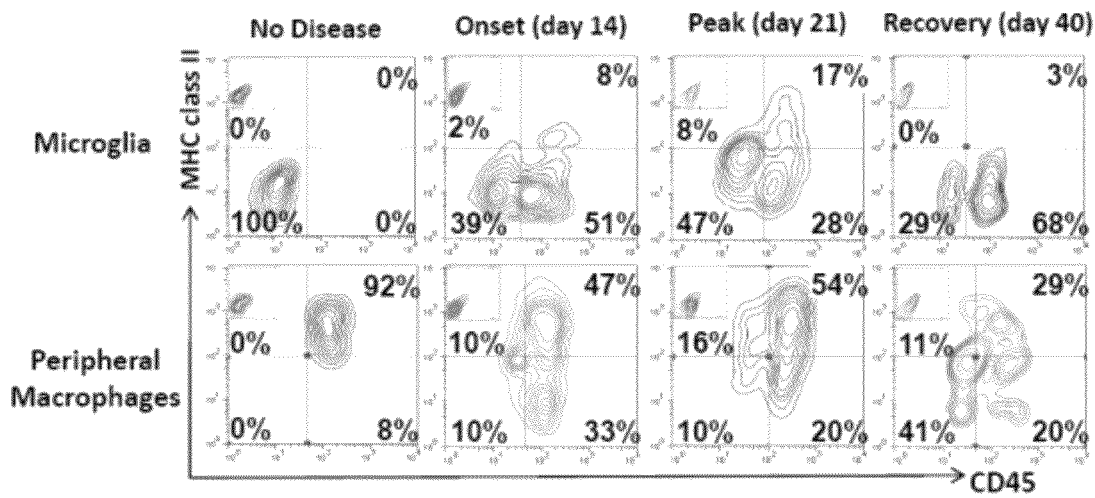
FIG. 2a is a set of eight graphs showing that activated microglia downregulate miR-124 both in vivo and in vitro. Mononuclear cells from a group of 4-5 healthy chimeric mice (no disease) or mice with EAE were isolated at onset (day 14), peak (day 21), and recovery (day 40) and analyzed for the expression of GFP, CD11b, F4/80, CD45, and MHC class II by five-color flow cytometry. Populations of gated F4/80$^+$CD11b$^+$GFP$^-$ microglia (upper row) and F4/80$^+$CD11b$^+$GFP$^+$ peripheral macrophages (lower row) are shown. The isotype controls are shown in upper left quadrants of contour-plots.

DETAILED DESCRIPTION microRNAs (miRNAs) are small single-stranded RNA molecules of the size of about 19-23 nucleotides. miRNAs belong to non-coding RNAs and are not translated into protein but regulate gene expression. Primary transcripts of miRNAs are processed into a short stem-loop structure called a pre-miRNA in the nucleus of the cell. The pre-miRNA forms a complex with a transport protein and is transported outside of the nucleus. The pre-miRNA is then processed into mature functional miRNA by cleavage mediated by Dicer. The mature miRNA is then incorporated into protein complexes, termed miRNPs, and the miRNPs have the ability to bind several messenger RNA (mRNA) molecules, which are also called "target" genes. The main function of binding of miRNAs to mRNA is to down-regulate the expression of these genes. Approximately 1,000 different miRNAs are predicted for mammalian cells, and each of them can potentially regulate expression of hundreds of genes (Ding et al., Trends Biotechnol. 27:27-36 (2009); Zhang and Su, J. Genet. Genomics 36:1-6 (2009)).

Mammalian miRNAs bind to sites in the 3' end of untranslated terminal region (UTR) of the mRNA. The annealing of the miRNA to the mRNA then inhibits protein translation, and may also facilitate cleavage of the mRNA in a mechanism similar to that of synthetic small interfering RNA or siRNA. microRNAs can also be viewed as natural analogs for siRNAs (Bi et al., Cell Physiol. 218:467-72 (2009)).

The activity of a miRNA can be visualized and experimentally blocked using fluorescently labeled locked nuclear acid (LNA) oligonucleotides, which covalently bind to specific microRNAs. Expression of miRNAs can be also quantitatively measured by real time quantitative polymerase chain reaction (qRT-PCR) using specific DNA probes (primers) that comprise complementary RNA-DNA duplexes (Naguibneva et al., Biomed. Pharmacother. 60:633-8 (2006)).

Dysregulation of miRNA is likely to be associated with disease pathology. The present disclosure describes the dysregulation of miR-124 in mice with experimental autoimmune encephalomyelitis (EAE), which is a mouse model for multiple sclerosis (MS), a central nervous system (CNS) inflammatory disease. Specifically, miR-124 expression is decreased in microglia in EAE mice. Systemic administration of miR-124 to EAE mice resulted in inhibition of EAE symptoms and downmodulation of CNS inflammation.

Thus, provided are methods of treating, reducing the risk of developing, or delaying the onset of a central nervous system (CNS) inflammatory disease in a subject. The methods comprise providing a subject with or at risk of developing a CNS inflammatory disease; and administering to the subject an effective amount of a therapeutic composition comprising miR-124 or a precursor thereof.

Also provided are methods of treating, reducing the risk of developing, or delaying the onset of an autoimmune disease in a subject. The methods comprise providing a subject with or at risk of developing an autoimmune disease; and administering to the subject an effective amount of a therapeutic composition comprising miR-124 or a precursor thereof Further provided are methods of identifying a subject with or at risk of developing a CNS inflammatory disease. The methods comprise obtaining a neural biological sample comprising a microglial cell from the subject to be tested; obtaining the microglial cell from the neural biological sample; and measuring a level of expression of miR-124 in the microglial cell. A decrease in the level of miR-124 expression as compared to a control indicates the subject has or is at risk for developing a CNS inflammatory disease.

miRNA Sequences miRNA 124 sequences are disclosed in miRBase, available on the internet at microrna.sanger.ac.uk/sequences/ and these sequences and others are herein incorporated by reference in their entireties as are individual subsequences or fragments contained therein. As used herein, miR-124 refers to the mature miR-124 sequence and homologs, variants, and isoforms thereof. For example, the nucleotide sequence of miR-124 is 5'-UAAGGCACGCGGUGAAUGCC-3' (SEQ ID NO:1). The same sequence is found in mouse, human, and rat. Stem-loop sequences from human, mouse, and rat miR-124 precursors are shown in FIG. 11.

In some embodiments, the methods described herein include administering, in addition to or as an alternative to miR-124, mR-506, which is homologous to miR-124 and is likely to function on the same targets as mir-124, or a precursor thereof. The sequence of mature>hsa-miR-506 (MIMAT0002878) is UAAGGCACCCUUCUGAGUAGA (SEQ ID NO:XX). The sequence of the miR-506 stem loop precursor is shown in FIG. 11.

In some embodiments, the methods described herein include administering, in addition to or as an alternative to miR-124, siRNA or antisense oligonucleotides directed to CCAAT/enhancer-binding protein alpha (CEBPa). In general, the methods described herein can use dsRNA molecules targeting CEPBa comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be designed using any method known in the art, and can include gene walk methods. The sequences of mouse CEBPa are known in the art, e.g., GenBank Acc. Nos. NM_007678.3 (nucleic acid) and NP_031704.2 (protein). The sequences of human CEBPa are known in the art, e.g., GenBank Acc. Nos. NM_004364.3 (nucleic acid) and NP_004355.2 (protein). siRNA sequences targeting CEBPa are known in the art, e.g., Sense, 5'-CCGCUCCAAUGCCU ACUGAtt-3' (SEQ ID NO:17); Antisense, 5'-UCAGUAGGCAUUGGAGCGGtg-3' (SEQ ID NO:18, Ambion) (see Zhang et al., Oncogene. Feb. 4, 2010; 29(5):723-38. Epub Nov. 9, 2009). Three pairs of complementary siRNA oligonucleotides against C/EBPa (C1-3) were synthesized by Invitrogen (Shanghai, China). Their target sequences for C/EBPa were 5'-GAACAGCAAC-GAGTACCGG-3' (SEQ ID NO:19) for C1, 5'-CCTTGTGC-CTTGGAAATGC-3' (SEQ ID NO:20) for C2, and 5'-CACT-TGTATCTGGCCTCTG-3' (SEQ ID NO:21) for C3 (see Zhao et al., PLoS One. Aug. 7, 2009; 4(8):e6552). Dhawan et al. further reported the following sequences of oligonucleotides used to knockdown C/EBPa expression: sense, 5'-GUCGGCCAGGAACUCGUCGUU-3' (SEQ ID NO:22) and antisense, 3'-UUCAGCCGGUCCUUGAGCAGC-3' (SEQ ID NO:23) (Dhawan et al., J Biol Chem. Jan. 30, 2009; 284(5):3086-95. Epub Dec. 3, 2008. Erratum in: J Biol Chem. Mar. 20, 2009; 284(12):8208). The methods of delivery and modifications described herein for miR-124 can equally be applied to miR-506 or siRNA for CEBPa.

The methods described herein can include the use of nucleotide sequences of miR-124 or a precursor thereof, or a variant that comprise a nucleotide sequence at least about 80%, 85%, 90%, 95%, 98%, 99% or more identical to the nucleotide sequence of miR-124 or a precursor thereof. Those of skill in the art readily understand how to determine the identity of two nucleic acid sequences. For example, the identity can be calculated after aligning the two sequences so that the identity is at its highest level.

Sequence identities can also be obtained for nucleic acids by, for example, the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989, which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and to be disclosed herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

miRNA Administration

Administration of miRNAs can occur via multiple routes. miRNAs can be chemically synthesized and administered to the cell, or miRNAs can be encoded in a nucleic acid sequence that is expressed in the cell via a DNA-based expression vector.

A chemically synthesized miRNA can comprise a ssRNA or dsRNA molecule. The RNA molecule can comprise the pri-miRNA, which can be hundreds of nucleotides in length, a pre-miRNA, which is generally 60-80 nucleotides in length (e.g., the stem-loop sequences shown in FIG. 11), or the mature miRNA, which is generally 18-23 nucleotides in length. Administration of the pri-miRNA and pre-miRNA to the cell results in production of the mature miRNA. RNA molecules can be synthesized in vitro from a DNA template, or can be synthesized commercially and are available from such corporations as Dharmacon, Inc. (Lafayette, Colo.), Qiagen (Valencia, Calif.), and Ambion (Austin, Tex.). In some embodiments, the miRNA is a synthetic miR-124 duplex that mimics pre-miR-124 (sense 5'-UAAG-GCACGCGGUGAAUGCC-3' (SEQ ID NO:1), antisense: 3'-UUAUUCCGTGCGCCACUUAC-5' (SEQ ID NO:12), Applied Biosystems)

The methods described herein can use both miRNA and modified miRNA derivatives, e.g., miRNAs modified to alter a property such as the specificity and/or pharmacokinetics of the composition, for example, to increase half-life in the body, e.g., crosslinked miRNAs. Thus, the invention includes methods of administering miRNA derivatives that include miRNA having two complementary strands of nucleic acid, such that the two strands are crosslinked. The oligonucleotide modifications include, but not limited to, 2'-O-methyl, 2'-fluoro, 2'-O-methyoxyethyl and phosphorothioate, boranophosphate, 4'-thioribose. (Wilson and Keefe, Curr. Opin. Chem. Biol. 10:607-614 (2006); Prakash et al., J. Med. Chem. 48:4247-4253 (2005); Soutschek et al., Nature 432:173-178 (2004)).

In some embodiments, the miRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying miRNA derivatives in this way may improve cellular uptake or enhance cellular targeting activities of the resulting miRNA derivative as compared to the corresponding miRNA, are useful for tracing the miRNA derivative in the cell, or improve the stability of the miRNA derivative compared to the corresponding miRNA.

The miRNA nucleic acid compositions can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., Drug Deliv. Rev. 47(1):99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles). The miRNA nucleic acid molecules can also be labeled using any method known in the art; for instance, the miRNA nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the miRNA can be radiolabeled, e.g., using $^3$H, $^{32}$P, or other appropriate isotope.

In general, synthetic siRNA or miRNA can be delivered using different approaches including cell penetrating peptides, proteamine-antibody fusion proteins, atelocollagen, cholesterol conjugation and stable nucleic acid-lipid particles, and phosphorothioate (PS)-stimulated uptake (see Detzer et al., Current Pharmaceutical Design, 2008, 14, 3666-3673, and references cited therein).

Liposomes and nanoparticles can be used to deliver miRNA into animals. Delivery methods using liposomes, e.g. stable nucleic acid-lipid particles (SNALPs), dioleoyl phosphatidylcholine (DOPC)-based delivery system, as well as lipoplexes, e.g. Lipofectamine 2000, TransIT-TKO, have been shown to effectively repress target mRNA (de Fougerolles, Human Gene Ther. 19:125-132 (2008); Landen et al., Cancer Res. 65:6910-6918 (2005); Luo et al., Mol. Pain 1:29 (2005); Zimmermann et al., Nature 441:111-114 (2006)). Conjugating miRNA to peptides, RNA aptamers, antibodies, or polymers, e.g. dynamic polyconjugates, cyclodextrin-based nanoparticles, atelocollagen, and chitosan, can improve miRNA stability and/or uptake. (See, e.g., Howard et al., Mol. Ther. 14:476-484 (2006); Hu-Lieskovan et al., Cancer Res. 65:8984-8992 (2005); Kumar, et al., Nature 448:39-43; McNamara et al., Nat. Biotechnol. 24:1005-1015 (2007);

Rozema et al., Proc. Natl. Acad. Sci. U.S.A. 104:12982-12987 (2007); Song et al., Nat. Biotechnol. 23:709-717 (2005); Soutschek (2004), supra; and Wolfrum et al., Nat. Biotechnol. 25:1149-1157 (2007)). See also Akinc et al., Nat Biotechnol. May 2008; 26(5):561-9; Schroeder et al., J Intern Med. January 2010; 267(1):9-21; Wang et al., "Delivery of siRNA Therapeutics: Barriers and Carriers," AAPS J. Jun. 11, 2010.

In some embodiments, the miRNA is delivered orally, e.g., in a preparation for oral delivery, see, e.g., Aouadi et al., Nature. Apr. 30, 2009; 458(7242): 1180-1184. Methods for preparing oral compositions are known in the art.

The therapeutic compositions comprising miRNAs described herein can include nucleic acid molecules encoding a miRNA, e.g., miR-124. Nucleic acid molecules encoding miRNAs are useful, e.g., where an increase in the expression and/or activity of a miRNA is desirable. Nucleic acid molecules encoding miR-124, optionally comprising expression vectors, can be used, e.g., for in vivo or in vitro expression of a selected miRNA. In some embodiments, expression can be restricted to a particular cell types so as to reconstitute the function of the selected miRNA in a cell, e.g., a cell in which that miRNA is misexpressed.

A nucleic acid encoding the selected miRNA can be inserted in an expression vector, to make an expression construct. A number of suitable vectors are known in the art, e.g., viral vectors including recombinant retroviruses, adenovirus, adeno-associated virus, and herpes simplex virus-1, adenovirus-derived vectors, or recombinant bacterial or eukaryotic plasmids. For example, the expression construct can include: a coding region; a promoter sequence, e.g., a promoter sequence that restricts expression to a selected cell type (i.e., a microglial-specific promoter, which can include a macrophage colony-stimulating factor (M-CSF) (c-fms) protooncogene promoter or a macrophage marker F4/80 promoter), a conditional promoter, or a strong general promoter; an enhancer sequence; untranslated regulatory sequences, e.g., a 5'-untranslated region (5'-UTR), a 3'-UTR; a polyadenylation site; and/or an insulator sequence. Such sequences are known in the art, and the skilled artisan would be able to select suitable sequences. See, e.g., Current Protocols in Molecular Biology, Ausubel, F. M. et al. (eds.) Greene Publishing Associates, (1989), Sections 9.10-9.14 and other standard laboratory manuals.

Expression constructs can be administered in any biologically effective carrier, e.g. any formulation or composition capable of effectively delivering the component gene to cells in vivo. Viral vectors transfect cells directly; plasmid DNA can be delivered with the help of, for example, cationic liposomes (e.g., Lipofectin) or derivatized (e.g. antibody conjugated), polylysine conjugates, gramicidin S, artificial viral envelopes or other such intracellular carriers, as well as direct injection of the gene construct or $CaPO_4$ precipitation. In some embodiments, the nucleic acid is applied "naked" to a cell, i.e., is applied in a simple buffer without the use of any additional agents to enhance uptake. See, e.g., Current Protocols in Molecular Biology, Ausubel, F. M. et al. (eds.) Greene Publishing Associates, (1989), Sections 9.10-9.14 and other standard laboratory manuals.

In clinical settings, the nucleic acids encoding miR-124 can be introduced into a patient by any of a number of methods known in the art. For instance, a pharmaceutical preparation comprising the nucleic acid delivery system can be introduced systemically, e.g. by intravenous injection, and specific transduction of the miRNA in the target cells occurs predominantly from specificity of transfection provided by the gene delivery vehicle, cell-type or tissue-type expression due to the transcriptional regulatory sequences controlling expression of the miRNA, or a combination thereof. In some embodiments, initial delivery of the miRNA is more limited with introduction into the animal being quite localized. For example, the miRNA delivery vehicle can be introduced by catheter (see U.S. Pat. No. 5,328,470) or by stereotactic injection (e.g. Chen et al. (1994) PNAS 91: 3054-3057).

Pharmaceutical Compositions and Methods of Administration

The methods described herein include the manufacture and use of pharmaceutical compositions. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Administration of the pharmaceutical compositions can be systemic. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. Parenteral preparations can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajimsa et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996). To facilitate delivery of miRNAs to the CNS, conjugation of stabilized RNA linked with cholesterol can also be used (e.g., as described in Czech, N. Engl. J. Med. 354:1194 (2006)).

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In some embodiments, the miRNA sequence includes a cell-penetrating peptide sequence that facilitates delivery of the miRNA to the intracellular space, e.g., HIV-derived TAT peptide, penetratins, transportans, or hCT derived cell-penetrating peptides, see, e.g., Caron et al., Mol. Ther. 3(3):310-8 (2001); Langel et al, *Cell-Penetrating Peptides: Processes and Applications* (CRC Press, Boca Raton, Fla.) (2002); El-Andaloussi et al., Curr. Pharm. Des. 11(28):3597-611 (2005); and Deshayes et al., Cell. Mol. Life Sci. 62(16):1839-49 (2005).

The pharmaceutical compositions can be included in a container, pack, or dispenser together with instructions for administration.

Methods of Treatment, Reducing the Risk, and Delaying the Onset of Disease

The methods described herein include methods for the treatment, reduction of risk, and delaying of onset of an autoimmune disease, e.g., a central nervous system (CNS) inflammatory disease. In some embodiments, the disease can be, e.g., multiple sclerosis (MS), experimental autoimmune encephalomyelitis (EAE), Alzheimer's, amyotrophic lateral sclerosis (ALS), or Parkinson's. In some embodiments, the disease is an autoimmune disease characterized by activation of microglia/macrophages, e.g., rheumatoid arthritis, type I and II diabetes, atherosclerosis and ALS. See, e.g., Wilson et al., Curr Vasc Pharmacol. April 2009; 7(2):234-43; Boillee and Cleveland, J Clin Invest. February 2008; 118(2):474-8; Kim and Lee, Current Molecular Medicine 2009, 9, 30-44; Olefsky and Glass, Annu. Rev. Physiol. 2010. 72:219-46; Ma and Pope, Current Pharmaceutical Design, 2005, 11, 569-580 569. Generally, the methods include administering a therapeutically effective amount of a first therapeutic composition comprising miR-124, as described herein, to a subject who is in need of, or who has been determined to be in need of, such treatment.

Also, the methods described herein include methods for the treatment, reduction of risk, and delaying of onset of an autoimmune disease. A number of autoimmune diseases that may be treated using the methods described herein are described in Rose and Mackay, The Autoimmune Diseases, Acadmic Press, San Diego, Calif. (1998). Examples of autoimmune diseases include, but are not limited to, Alopecia Areata, Lupus, Ankylosing Spondylitis, Meniere's Disease, Antiphospholipid Syndrome, Mixed Connective Tissue Disease, Autoimmune Addison's Disease, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinemia Sarcoidosis, Fibromyalgia, Scleroderma, Grave's Disease, Sjögren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Diabetes (Type II), Vasculitis, Lichen Planus, and Vitiligo.

As used herein the terms "treatment", "treat", or "treating" refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms "reducing the risk of" or "delaying the onset of" a disease or disorder refers to an action, for example, administration of a therapeutic agent, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

Dosage, toxicity and therapeutic efficacy of the compounds can be determined, e.g., by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The methods and compositions as described herein are useful for both prophylactic and therapeutic treatment. For prophylactic use, a therapeutically effective amount of the agents described herein are administered to a subject prior to onset (e.g., before obvious signs of a CNS inflammatory disease to a subject identified as being at risk of developing the disease, e.g., based on one or more risk factors as are known in the art) or during early onset (e.g., upon initial signs and symptoms of a CNS inflammatory disease). Prophylactic administration can occur for several days to years prior to the manifestation of symptoms of osteoarthritis. Prophylactic administration can be used, for example, in the preventative treatment of subjects diagnosed with a genetic predisposition to a CNS inflammatory disease. Therapeutic treatment involves administering to a subject a therapeutically effective amount of the agents described herein after diagnosis or development of a CNS inflammatory disease.

An "effective amount" is an amount sufficient to effect beneficial or desired results. For example, a therapeutic amount is one that achieves the desired therapeutic effect, e.g., an improvement in a clinical parameter of the disease. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

As used throughout a "subject" can be a vertebrate, e.g., a mammal (e.g., a human, horse, cat, dog, cow, pig, sheep, goat, mouse, rabbit, rat, and guinea pig). The term does not denote a particular age or sex. Thus, adult and newborn subjects, whether male or female, are intended to be covered. As used herein, patient or subject may be used interchangeably and can refer to a subject with a disease or disorder (e.g. a CNS inflammatory disease). The term patient or subject includes human and veterinary subjects.

Those of skill in the art understand that the administration of a first therapeutic composition comprising miR-124 requires that the miR-124 sequence correspond to the species of subject being treated with miR-124. For example, if the subject is human, the miR-124 sequence is SEQ ID NO:1.

A subject at risk of developing a disease or disorder can be genetically predisposed to the disease or disorder, e.g., have a family history or have a mutation in a gene that causes the disease or disorder, or show early signs or symptoms of the disease or disorder. A subject currently with a disease or disorder has one or more than one symptom of the disease or disorder and may have been diagnosed with the disease or disorder.

Methods of Diagnosis

Included herein are methods for diagnosing a subject with or at risk of developing a central CNS inflammatory disease. The methods include obtaining a neural biological sample comprising a microglial cell from a subject; obtaining the microglial cell from the neural biological sample; measuring a level of expression of miR-124 in the microglial cell; and comparing the presence and/or level with one or more references, e.g., a control reference that represents a normal level of miR-124, e.g., a level in an unaffected subject, and/or a disease reference that represents a level of miR-124 associated with a CNS inflammatory disease, e.g., a level in a subject having multiple sclerosis. A decrease in the level of miR-124 expression as compared to a control indicates the subject has or is at risk for developing a CNS inflammatory disease. The presence and/or level of a miRNA can be evaluated using methods known in the art, e.g., using RNA expression assays, e.g., microarray analysis, RT-PCR, deep sequencing (Huang et al., "DSAP: deep-sequencing small RNA analysis pipeline," Nucleic Acids Res. May 13, 2010; Schulte et al., "Deep sequencing reveals differential expression of microRNAs in favorable versus unfavorable neuroblastoma," Nucleic Acids Res. May 13, 2010), cloning (Landgraf et al., Cell. Jun. 29, 2007; 129(7):1401-14), Northern blot, and quantitative real time polymerase chain reaction (qRT-PCR). Analytical techniques to determine RNA expression are known. See, e.g., Sambrook et al., Molecular Cloning: A Laboratory Manual, 3$^{rd}$ Ed., Cold Spring Harbor Press, Cold Spring Harbor, N.Y. (2001).

A further confirmation of diagnosis can, for example, include determining the level of expression of CEBPα in the microglial cell. An increase in the level of CEBPα expression as compared to a control indicates the subject has or is at risk for developing a CNS inflammatory disease. Determining the level of CEBPα can include determining the level of RNA or protein expression. RNA expression can be determined as described above. Protein expression can be determined by using an assay selected from the group consisting of a Western blot, an enzyme-linked immunosorbent assay (ELISA), an enzyme immunoassay (EIA), radioimmunoassay (RIA), or protein array. Analytical techniques to determine protein expression are known. See, e.g., Sambrook et al., Molecular Cloning: A Laboratory Manual, 3rd Ed., Cold Spring Harbor Press, Cold Spring Harbor, N.Y. (2001).

EXAMPLES

The invention is further described in the following examples, which do not limit the scope of the invention described in the claims.

Methods

The following methods were used in the Examples set forth below.

Mice.

B6 (C57BL/6), CX3CR1-GFP (B6.129P-Cx3cr1$^{tm1Litt}$/J) CEBPA$^{F/F}$ (B6.Cg-Cebpa$^{tm1Dgt}$ Tg(Mx1-cre)1Cgn/J) and ACTB-GFP Tg (C57BL/6-Tg(ACTB-EGFP)131Osb/Ley-SopJ) mice were purchased from Jackson Laboratories. MOG-TCR transgenic 2D2 mice were maintained in the inventors' colony.

Antibodies, Cytokines, and Peptides.

The fluorochrome-conjugated antibodies for CD11b, CD11c, CD205, F4/80, MHC class II, CD86, CD4, CD3, CD69, CD25, CD44, CD62L, B220, CD19, IL-6, TNFα and IFNγ were purchased from BD Biosciences, eBioscience, and Biolegend. Anti-CEBPα antibodies were purchased from Epithomics and anti-PU.1 from Cell Signaling Technology. MOG$_{35-55}$ peptide was purchased from Sigma. All cytokines were purchased from R&D Systems.

Macrophage Cell Culture.

Bone marrow was isolated from B6, CEBPA$^{F/F}$ or ACTB-GFP Tg mice 4-6 weeks old; after lysis of erythrocytes, mononuclear cells were incubated with M-CSF (10 ng/ml) in DMEM media (ATCC) supplemented with 10% FBS for 5 days. The medium was changed every 2-3 days.

Dendritic Cell Culture.

Bone marrow and stromal cells were isolated from 4-6 week old B6 mice; erythrocytes lysed, and the cells incubated with GM-CSF (50 ng/ml) in DMEM media supplemented with 10% FBS for 5 days. The medium was changed every 2-3 days. To induce maturation, the cells were incubated with LPS (100 ng/ml) for 24 hours prior to the analysis.

Isolation of Mononuclear Cells.

Mice were perfused intracardially with PBS prior to the dissection of the brain, spinal cord, or liver, which were homogenized; mononuclear cells were isolated using 40%/70% Percoll gradients. Peritoneal macrophages were isolated by peritoneal lavage of intact mice or after 5 days of single injection of 2 ml of 4% thioglycolate broth media.

RNA Isolation.

RNA was isolated using the "mirVana kit"™ according to the manufacturer's instructions (Applied Biosystems).

Transfections and Injections of miR-124, Anti-miR-124 and siRNA.

50 nM of miR-124a duplex that mimics pre-miR-124a (sense 5'-UAAGGCACGCGGUGAAUGCC-3' (SEQ ID NO:1), antisense: 3'-UUAUUCCGTGCGCCACUUAC-5' (SEQ ID NO:12), Applied Biosystems), anti-miR-124 (LNA-containing antisense oligonucleotide, Exiqon Inc.) or a cocktail of three siRNAs for CEBPA (Applied Biosystems; Silencer® Select Pre-Designed & Validated siRNA, siRNA IDs:s63853, s63854, s63855) were used for in vitro transfections and 15-20 μg of the oligo per mouse for in vivo injections. miR-124 or anti-mir-124 were complexed with LIPOFECTAMINE 2000™ (Invitrogen) lipofection reagent according to manufacturer's instructions. As negative controls for miR-124 and anti-mir-124, control miRNA (Negative Control#1, sense: 5' AGUACUGCUUACGAUACGGTT 3' (SEQ ID NO:13), antisense: 5' CCGUAUCGUAAG-CAGUACUTT 3' (SEQ ID NO:14), Applied Biosystems), mutant miR-124 lacking binding sites for CEBPA (Applied Biosystems, sense: 5'-UUUCCGACGCGGUGAAUUCC-3' (SEQ ID NO:15), antisense: 3'-UUAAAGGCTGCGC-CACUUAA-5' (SEQ ID NO:16)) or control antagomir (Exiqon) were used. For overexpression of miR-124 in vitro, macrophages were transfected twice with miR-124 or control miRNA (the second transfection was performed on day 3 after the first transfection). For in vivo injections, 30 μl of Lipofectamine2000 was mixed with miR-124 or anti-miR-124 dissolved in 170 μl of PBS, and the liposome complexes were injected intravenously (200 μl/mouse) or intracranially (25 μl/mouse). Fluorescent Cy3-labeled miR-124 and negative control miRNA were purchased from Applied Biosystem, and FITC-labeled miR-124 inhibitor was from Exiqon Inc.

Analysis of miR-124 Expression.

For analysis of miRNA expression, real-time RT-PCR analyses were carried out using TaqMan miRNA assays (Applied Biosystems) and relative expression was calculated using the $\Delta C_T$ method as described elsewhere[5] and normalized to uniformly expressed snoRNA55 and snoRNA135 (Applied Biosystems). All qRT-PCRs were performed in triplicates, and the data are presented as mean±standard errors (S.E.).

Flow Cytometry and Cell Sorting.

1-5-color flow cytometry analysis was conducted following standard procedures. Flow cytometry analysis was conducted on the LSR II Cytometer, and cell sorting was performed in FACSAria (both from BD Biosciences). For intracellular staining for CEBPα. PU.1, IL-6, TNFγ or IFNγ the cells were stained for surface markers, and then fixed and permeabilized using reagents from BD BrdU Flow kit (BD Biosciences). Imaging cytometry was performed on IMAGESTREAM™ cytometer (Amnis Inc.) in Flow and Imaging Core Facility of Immune Disease Institute (Harvard Medical School).

Cell Proliferation.

Proliferation was assessed by flow cytometry examining bromodeoxyuridine (BrdU) labeling of cells in vivo and in vitro following addition of BrdU to cell cultures for 14 hours or i.p. injection of 1 mg BrdU prior to isolation of cells from spleen and CNS of mice with EAE. Analysis of BrdU labeling of cells was performed using the BD BrdU Flow kit from BD Biosciences.

CD4 T Cell Recall Response.

MOG-TCR transgenic 2D2 mice were immunized with 150 µg MOG in 4 mg/ml CFA in footpads, and seven days later CD4$^+$ T cells were isolated from spleen by negative selection using magnetic beads. CD4 T cells were incubated with irradiated splenocytes from B6 mice for 48 hours in the presence of $MOG_{35-55}$ (1-20 µg/ml), after which the level of proliferation was assessed as described above.

EAE Induction.

EAE was induced by subcutaneous immunization with 150 µg MOG or PLP in 4 mg/ml CFA of 8-12-week-old B6, $CEBPA^{F/F}$, chimeric, SJL or $IF\gamma^{-/-}$ mice. Pertussis toxin was given i.p. (150 ng/mouse) on days zero and two post-immunization. To conditionally knockout CEBPA gene in $CEBPA^{F/F}$ mice, animals were injected i.p. 100 µg/mouse poly I:C (Sigma) at indicated time points. Mice were observed for signs of disease starting on day five post-transfer, and disease severity was scored on a numerical scale from 0-5 as follows: 0) no disease; 1) weak tail or wobbly walk; 2) hind limb paresis; 3) hind limb paralysis; 4) hind and forelimb paralysis; and 5) death or euthanasia due to humane reasons.

Irradiation of BM Chimeras.

B6 or $CX3CR1^{GFP/+}$ mice (eight weeks old) were lethally irradiated (950 rads) and reconstituted with 7-10×10$^6$ total mononuclear BM cells from the $CX3CR1^{GFP/+}$ or B6 mice, respectively ($CX3CR1^{GFP/+}\rightarrow$B6 or B6$\rightarrow CX3CR1^{GFP/+}$ chimeras) and allowed to reconstitute for eight weeks. The percent of chimerism was determined at eight weeks post-transplant by the examining cells from the spleen as described previously[11]. 95-97% of F4/80$^+$CD11b$^+$ cells in the spleen were GFP positive. EAE was induced at eight-nine weeks post-BM transplantation.

Western Blot Analysis.

The cells were lysed by a standard procedure in RIPA buffer containing protease inhibitors (Roche Diagnostics). Protein concentrations of total cell lysates were measured using a Micro BCA protein assay kit (Pierce Biotechnology), and 50 µg per lane of total cell lysates was resolved on SDS electrophoresis gels (Invitrogen), followed by immunoblot visualization with ECL detection reagents (Pierce Biotechnology) Immunoblotting was performed with mouse anti-CEBP (Epitomics) and mouse anti-actin (Abcam) primary antibodies.

Luciferase Reporter Assay for Target Validation.

Mouse CEBPa 3'-UTR (823 bp) was amplified from a mouse genomic DNA library (New England Biolab) by PCR. The CEBPa 3' UTRs was cloned into the SpeI and HindIII sites of pMir-Report (Ambion) as described earlier[4,5]. Mutations were introduced in the potential miR-124 binding sites using a QuikChange site-directed mutagenesis kit (Stratagene). Mouse neuroblastoma NIE115 cells were transfected with the pMir-Report vectors containing the 3' UTR variants, and 5 hours after the transfections the cells were transfected again with 50 nM of either miR-124 or negative control miRNA. The cells were lysed and luciferase activity was measured 24 hours post-transfection. pRenilla was cotransfected and used for normalization.

Coculture Assay.

Bone Marrow-derived Macrophages (BM-MΦ) were obtained from ACTB-GFP Tg mice as described above and co-cultured for six days with astrocyte type IC8-D1A cell line or neuroblastoma NIE115 cells (both from ATCC) in DMEM media supplemented with 10% FBS and 10 ng/ml M-CSF. Neuroblastoma cells were induced to differentiate to neuronal-like cells by treatment with retinoic acid (10 µM, Sigma) in DMEM media with 10% FBS for three days prior to co-culture. After treatment media was replaced 2-3 time to remove retinoic acid before addition of macrophages for coculture.

Statistical Analysis.

Student's t-test was used to validate the significance of the observed differences. A p-value of less than 0.05 was considered statistically significant.

Example 1

MiR-124 is Highly Expressed by CNS-Resident Microglia

To identify miRNAs that are enriched in microglia, 31 miRNAs known to be expressed in immune cells and in the CNS[22] were selected and their expression was analyzed in sorted CD11b$^+$F4/80$^+$ macrophages from different organs of healthy adult mice by real-time qRT-PCR (Table 1).

TABLE 1

Selective profiling of microRNA expression in microglia in comparison with monocytes and peripheral macrophages in normal mice[1] and mice with EAE.[2]

| miRNA | No Disease | | EAE (Peak of Disease) |
|---|---|---|---|
| [Microglia]/ | [Macrophage]/ | [Microglia]/[Peripheral |
| [Monocyte] Ratio[3] | [Monocyte] Ratio[4] | Macrophage] Ratio[5] |
| Thioglicolate Macrophages | | BM-derived Macrophages | |
| miR-124a * | 210 | 0 | 0 | 48[6,7] |
| mR-223 * | 0.005 | 1.3 | 0.6 | 10 |
| miR-192 ** | 0.1 | 7 | 0.7 | 9 |
| miR-21 ** | 0.1 | 9 | 10 | 2 |
| miR-221 ** | 0.05 | 1.2 | 30 | 2 |
| miR-150 ** | 0.03 | 3.8 | 0 | 2 |
| miR-142-5p ** | 0.2 | 0 | 0.6 | 1.8 |
| miR-27a ** | 0.4 | 1.3 | 3.9 | 1.7 |
| miR-200c | 0.07 | 0.7 | 0.7 | 1.6 |
| miR-93 | 0.06 | 0.2 | 0.5 | 1.3 |
| miR-106a | 0.1 | 0.4 | 0.5 | 1.3 |
| miR-106b | 0.1 | 0.6 | 0.5 | 1.3 |
| miR-17-5p | 0.06 | 0.3 | 0.5 | 1.1 |
| miR-27b | 0.2 | 0.7 | 12 | 1.1 |
| miR-146 | —[8] | — | — | 1.0 |
| miR-124b | 1.8 | 0.6 | 0.2 | 0.9 |
| miR-191 | 0.1 | 0.5 | 0.5 | 0.9 |
| miR-200a | ND[9] | ND | ND | 0.8 |
| miR-23a | 0.5 | 3 | 5 | 0.8 |
| miR-296 *** | 0.8 | 4.3 | 4.2 | 0.6 |
| miR-125b *** | 12 | 7 | 10 | 0.4 |

TABLE 1-continued

Selective profiling of microRNA expression in microglia in comparison with monocytes and peripheral macrophages in normal mice[1] and mice with EAE.[2]

| miR-99a *** | 8 | 12 | 19 | 0.1 |
|---|---|---|---|---|
| miR-15a | ND | ND | ND | — |
| miR-25 | ND | ND | ND | — |
| miR-29a | ND | ND | ND | — |
| miR-33 | ND | ND | ND | — |
| miR-128a | 1.1 | 0.04 | 0.12 | — |
| miR-141 | ND | ND | ND | — |
| miR-142-3p | ND | ND | ND | — |
| miR-155 | ND | ND | ND | — |
| miR-215 | ND | ND | ND | — |

[1]Mononuclear cells were isolated from brains and peripheral blood of eight week-old adult B6 mice using Percoll and Ficoll gradients, respectively; thioglicolicolate and bone marrow (BM) - derived macrophages were obtained as described elsewhere (see Methods section for details). To assess microRNA expression, F4/80$_+$CD11b$_+$ cells were sorted by FACS, RNA was isolated and analyzed by real-time qPCR using specific primers for selected miRNAs.
[2]Chimeric mice were prepared as described herein, and after eight weeks of reconstitution EAE was induced. Mononuclear cells from chimeric mice with EAE were isolated at the peak of disease (day 21 after disease induction), and the cells were stained for macrophage markers CD11b and F4/80. Populations of F4/80$_+$CD11b$_+$GFP$_-$ microglia and F4/80$_+$CD11b$_+$GFP$_+$ macrophages were sorted, RNA was isolated, and microRNA expression was assessed by real-time RT-PCR
[3]Expression of particular miRNA in microglia isolated from normal brain was normalized to the expression of housekeeping snoR-55 and [microglial miRNA]/[monocyte miRNA] expression ratio is shown.
[4]Expression of particular miRNA in thioglicolate or BM-derived macrophages was normalized to the expression of housekeeping snoR-55 and [macrophage miRNA]/[monocyte miRNA] expression ratio is shown.
[5]Expression of particular miRNA in microglia was normalized to the expression of housekeeping snoR-55 and [microglial miRNA]/[peripheral macrophage miRNA] expression ratio is shown.
[6]The list of tested microRNA is organized in order of [microglial miRNA]/[peripheral macrophage miRNA] ratio (R) with the highest R ≥ 10 marked with one asterisk (*), R > 1.6 marked with two asterisks () and R ≤ 0.6 marked with three asterisks (*).
[7]$P < 0.001$
[8]Expression of microRNA is close or below the detection level detection by real-time qRT-PCR.
[9]Not Determined This analysis revealed that only resident macrophages from brain and spinal cord (microglia) expressed miR-124 (FIG. 1a), whereas myeloid-specific miR-223[6,23] was expressed in the macrophages in the periphery, but not in the microglia (FIG. 1b). The level of miR-124 expression in microglia was comparable to that in cultured cortical neurons (FIG. 1e-f), the cells expressing the highest miR-124 levels[22, 24, 25]. The next set of experiments further investigated expression of specific miRNAs, including miR-124, in microglia during experimental autoimmune encephalomyelitis (EAE), a disease characterized by microglia activation and infiltration of peripheral macrophages into the CNS. Since there are no markers to distinguish microglia from peripheral macrophages that migrate into the CNS during inflammation, chimeric animals were used to discriminate between these populations. In these chimeras, microglia and peripheral macrophages can be easily separated by FACS (FIGS. 1c and 1g), although peripheral macrophages may be contaminated by small numbers of GFP$^+$ microglia that enter the CNS during reconstitution[11]. miR-124 expression was measured in sorted populations of CD11b$^+$F4/80$^+$GFP$^-$ microglia and CD11b$^-$F4/80$^+$GFP$^+$ CNS-infiltrating peripheral macrophages of healthy chimeras and chimeric mice with EAE at different stages of disease (FIG. 1d and Table 1). In microglia, miR-124 expression decreased ~3-fold during the course of the disease (FIG. 1d, day 14, day 21 and day 40) when compared to healthy chimeras, (FIG. 1d, no disease). Peripheral macrophages however, began to express low levels of miR-124 during onset and at the recovery phase (FIG. 1d, day 14 and day 40). These results demonstrate that miR-124 is strongly expressed in microglia both in normal CNS and during EAE; it is undetectable in macrophages in the periphery, but is slightly induced in CNS-infiltrating peripheral macrophages during the onset (d14) and recovery phases (d40) of the disease.

Example 2

Activated Microglia Down-Regulate miR-124

Figure 2B:
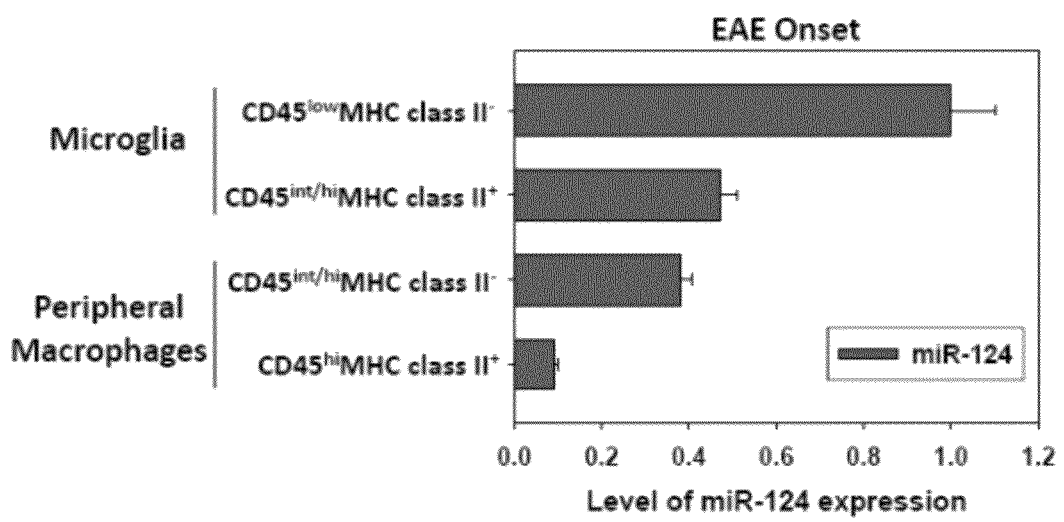
FIG. 2b is a bar graph showing populations of resting CD45$^{low}$MHC class II$^-$ GFP$^-$ and activated CD45$^{int/hi}$MHC class II$^+$GFP$^-$ microglia as well as populations of activated CD45$^{hi}$MHC class II$^+$GFP$^+$ and deactivated CD45$^{int/hi}$MHC class II$^-$GFP$^+$ peripheral macrophages sorted by FACS from the CNS of chimeric mice with EAE at day 14, and miR-124 expression was assessed by real-time RT-PCR. Representative results from two independent experiments are shown.

In the model described herein, microglia in healthy chimeric mice had a CD45$^{low}$MHC class II$^-$ phenotype (FIG. 2a, no disease), while during onset and peak of EAE, microglia up-regulated CD45 and MHC class II (FIG. 2a, onset and peak). During recovery, the level of MHC class II in microglia returned to normal, but a subset of cells remained CD45$^{hi}$, suggesting some residual level of activation. Peripheral macrophages in CNS of healthy mice exhibited an activated CD45$^{hi}$MHC class II$^{hi}$ phenotype, which was consistent with previous studies demonstrating that BM-derived macrophages in normal CNS have a perivascular location and exhibit an activated phenotype[26]. Most of the peripheral macrophages that infiltrate the CNS during EAE onset and at the peak of disease also exhibited activated CD45$^{hi}$MHC class II$^-$ phenotype (FIG. 2a, onset and peak). During onset of EAE ~30% of peripheral macrophages exhibited a partially deactivated CD45$^{hi/int}$MHC class II-phenotype (FIG. 2a), while during recovery 41% of peripheral macrophages became CD45$^{low}$MHC class II– (FIG. 2a, recovery), suggesting further deactivation. This finding is in agreement with recent studies demonstrating the appearance of BM-derived cells in the CNS during inflammation, which have phenotypical features of microglia[27]. The miR-124 expression pattern (down-regulation in microglia at EAE onset when the cells become activated, and up-regulation in peripheral macrophages at EAE onset and recovery when the subset of cells deactivates) (FIG. 1d and FIG. 2a, day 14 and day 40) suggests a link between miR-124 and the microglia/macrophage activation state. Therefore the levels of miR-124 expression were further compared in populations of resting CD45$^{low}$ MHC class II– microglia, activated CD45$^{int/hi}$MHC class II+ microglia (MHC class II positive microglia have intermediate or high level of CD45 expression), activated CD45$^{hi}$MHC class II+ peripheral macrophages and deactivated CD45$^{int/hi}$MHC class II$^-$ macrophages (MHC class II negative macrophages have intermediate or high level of CD45 expression) sorted from the CNS of mice with EAE (onset of disease). The highest level of miR-124 expression was observed in resting CD45$^{low}$MHC class II– microglia, while activated MHC class II+ microglia expressed a 2.5-fold lower level of miR-124 (FIG. 2b, Microglia). Activated MHC class II+ peripheral macrophages expressed very low levels of miR-124, while deactivated MHC class II– macrophages up-regulated miR-124 by 4.2-fold (FIG. 2b, Peripheral Macrophages).

Figure 2C:
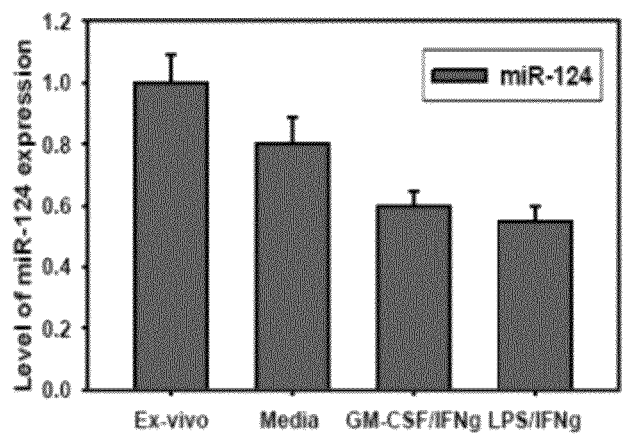
FIG. 2c is a bar graph showing miR-124 expression in microglia cells isolated from healthy mice and incubated in media alone or with GM-CSF and IFNγ, or LPS and IFNγ for six hours, after which RNA was isolated and miR-124 was assessed by real-time PCR.

To investigate whether activated microglia had down-regulated miR-124 in vitro, microglia isolated from healthy adult mice were cultured for six hours in media alone, GM-CSF/IFNγ, or LPS/IFNγ. Microglia cultured with GM-CSF/IFNγ or LPS/IFNγ had down-regulated miR-124 when compared to ex-vivo isolated cells or cells cultured in media alone (FIG. 2c). There was also a decrease in miR-124 expression in cultured microglia compared to ex-vivo isolated cells (FIG. 2c), which was likely due to spontaneous activation of microglia in vitro. Cytokine milieu did not affect the viability of ex-vivo isolated microglial cells as determined by vital dye staining with 7AAD. Thus, these data demonstrate that activated microglia have down-regulated miR-124 both in vivo and in vitro.

Figure 2D:
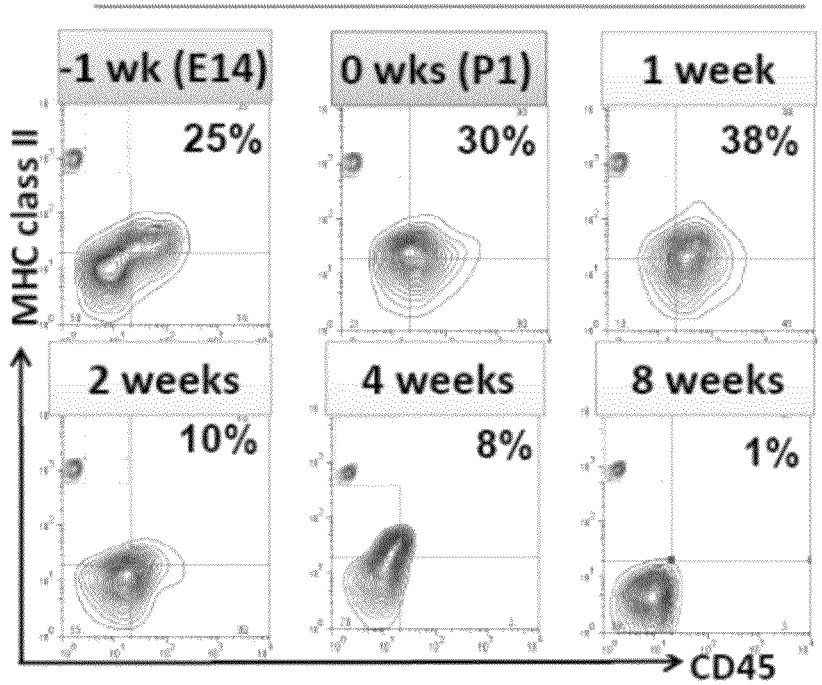
FIGS. 2d-e show that prenatal and neonatal microglia exhibit an activated phenotype and express lower levels of miR-124 compared to adult microglia. Brains from mice on embryonic day E14 (one week before birth or −1 week), 1-2 days old (0 weeks), 1, 2, 4, and 8 week-old were dissected, and mononuclear cells isolated and stained for CD11b, CD45, and MHC class II. All mice except E14 embryos were perfused intracardially with PBS before brain dissections. The expression of MHC class II and CD45 is shown for CD11b+ gated cells in the FACS results in 2d. The expression of miR-124 in CD11b+ sorted cells was measured by qRT-PCR and is shown in bar graph form in 2e.
Figure 2E:
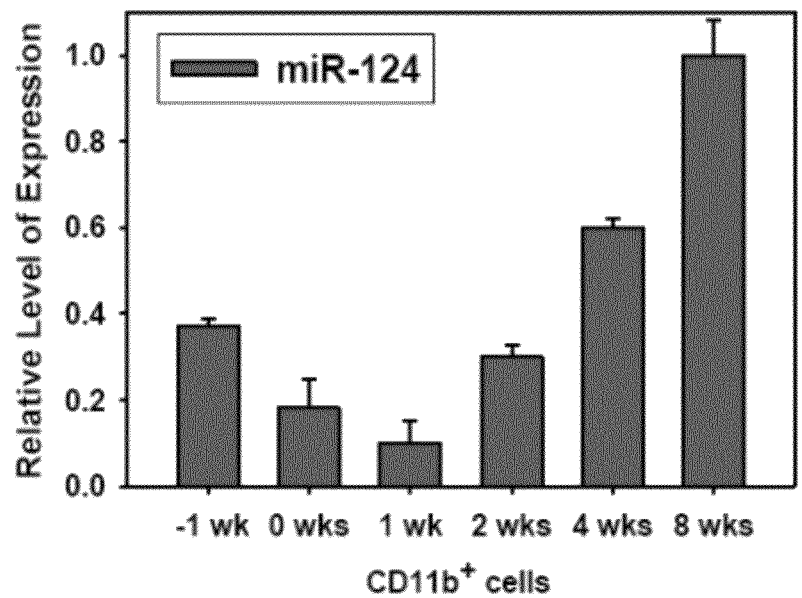

It has been reported that macrophages populate the brain in two waves, before and shortly after birth, and exhibit an activated phenotype in neonates[12,28]. Since activated microglia have down-regulated miR-124, the kinetics of activation marker and miR-124 expression were investigated during different stages of development. In mice, four weeks old and younger, microglia exhibited elevated levels of expression of MHC class II and CD45, with the highest percentages of cells exhibiting a CD45$^{hi}$MHC class II$^+$ phenotype in newborn mice (FIG. 2d). In parallel, it was determined that miR-124 expression reached its maximal level in microglia by 8-week of development while the lowest expression was observed in newborn animals (FIG. 2e). These data indicate that in newborn mice microglia exhibit an activated phenotype and express low levels of miR-124; in adult mice microglia have down-regulated activation markers and up-regulated miR-124 expression. Collectively, these data demonstrate that miR-124 expression correlates inversely with the activation state of microglia/macrophages in the CNS.

Example 3

Figure 3A:
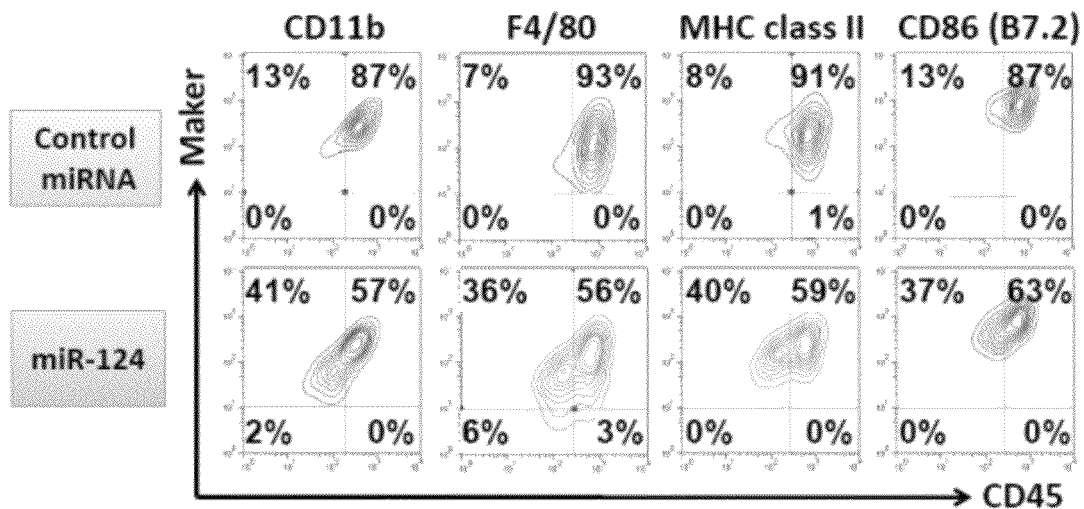
FIGS. 3a-b show that miR-124 overexpression in bone-marrow (BM)-derived macrophages in vitro causes down-regulation of expression of activation markers, decrease in proliferation, and morphological changes. BM-derived macrophages were expanded in culture with M-CSF for five days, transfected with miR-124 or control miRNA as described in Methods, and analyzed for the expression of CD45, CD11b, F4/80, MHC class II, and CD86 by FACS. A representative experiment is shown in FIG. 2a, and mean±S.E. of four independent experiments is shown in bar graph form in 2b. Asterisk (*) indicates that decreases in mean fluorescence intensity (MFI) for CD45, CD11b, F4/80, MHC class II, and CD86 are statistically significant (p<0.05).
Figure 3B:
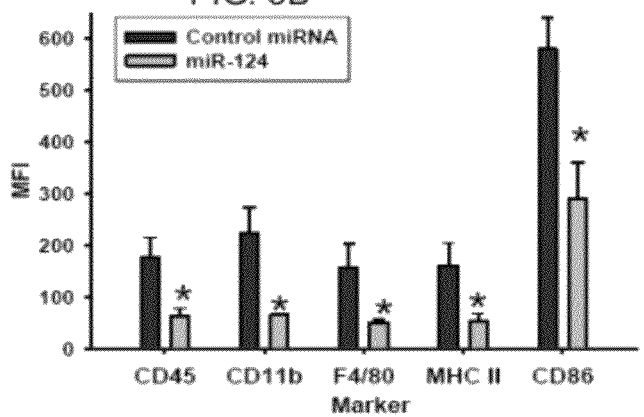
Figure 3C:
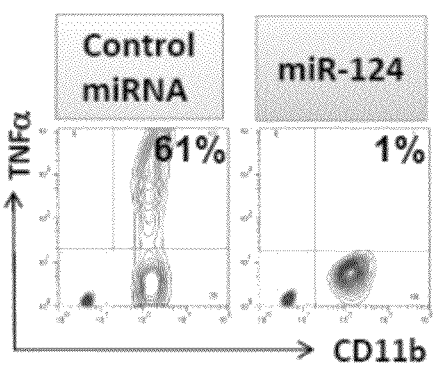
FIG. 3c is a pair of FACS panels showing that transfection of BM-derived macrophages resulted in inhibition of TNFα production by macrophages as determined by intracellular staining. Isotype controls are shown in the lower left quadrants.
Figure 3D:
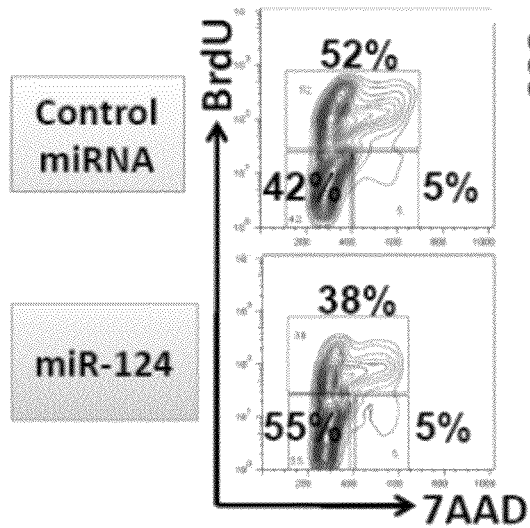
FIGS. 3d and 3f show results from FACS analysis of BM-derived macrophages transfected with miR-124 or control miRNA; BrdU was added to the cultures 16 hours prior to cell collection. Cells were stained for BrdU and DNA content and analyzed by FACS. A representative experiment is shown in 3d and the mean±S.E. of four independent experiments is shown in 3f. Two asterisks (**) indicate that increases in percentages of cells in G1/G0 phases and decreases in the percentage of cells in S-phases of cell cycle are statistically significant (p<0.01).
Figure 3E:
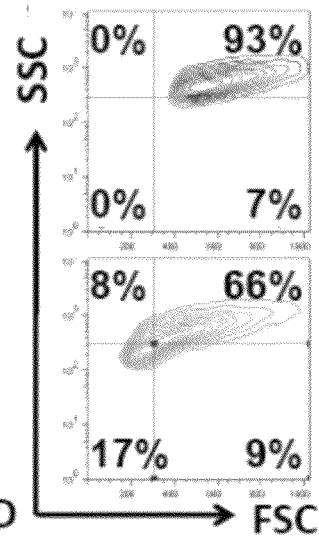
FIG. 3e is a pair of FACS plots showing that transfections of BM-derived macrophages resulted in changes in cell morphology (decrease in cell size) as determined by decrease in FSC/SSC parameters.
Figure 3F:
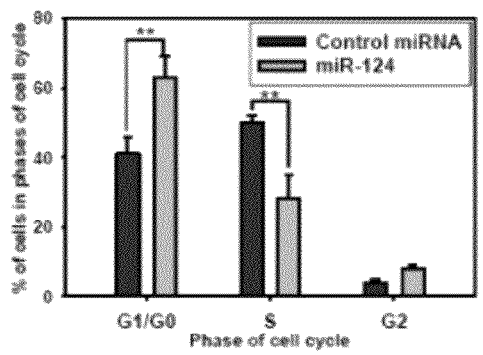
Figure 3G:
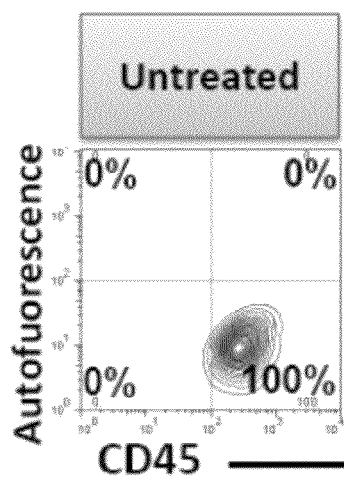
FIGS. 3g-i are FACS plots showing the distribution analysis of transfected fluorescently labeled miR-124 in bone marrow derived macrophages. BM-derived macrophages were expanded in culture with M-CSF for five days, the cells were transfected with fluorescent Cy3-labeled miR-124 (3h) or Cy3-labeled control miRNA (3i). The cells were harvested 48 hours post-transfection, stained with anti-CD45 antibody and analyzed for the expression of CD45 and Cy3 by FACS. Untreated macrophages were used as control in (3g).

Ectopic Expression of miR-124 Deactivates Bone Marrow-Derived Macrophages In Vitro The next series of experiments were performed to determine whether transfection of peripheral macrophages with miR-124 resulted in down-regulation of activation markers. Bone marrow-derived macrophages (BM-MΦ) were transfected with either miR-124 or negative control RNA as described in Methods. BM-MΦ transfected with negative control exhibited an activated phenotype with high levels of CD45, CD11b, F4/80, MHC class II, and CD86. Transfection of BM-MΦ with miR-124 resulted in substantial down-regulation of CD45 and less prominent but also significant down-regulation of CD11b, F4/80, MHC class II and CD86 (FIG. 3a). The quantification of the four experiments is shown in FIG. 3b. Transfection of macrophages with miR-124 also completely inhibited expression of TNFa by these cells in vitro as determined by intracellular staining (FIG. 3c). In addition, transfection with miR-124 resulted in a 2-fold decrease in the number of proliferating cells in S-phase as determined by BrdU incorporation and DNA content assay (FIG. 3d,f). In addition, miR-124-transfected cells had lower levels of forward scatter (FCS) and side scatter (SSC) when compared to control, which correspond to cell size and granularity, respectively (FIG. 3e). To verify that the decrease in cell size and granularity were not caused by cell death, 7AAD (stains DNA of dead cells) was added to these cultures. FCS$^{low}$SSC$^{low}$ cells were negative for 7AAD, while a small proportion of 7AAD$^+$ cells were SSC$^{hi}$ (data not shown).

Figure 3H:
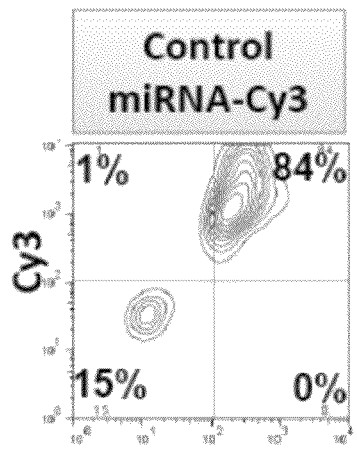
Figure 3I:
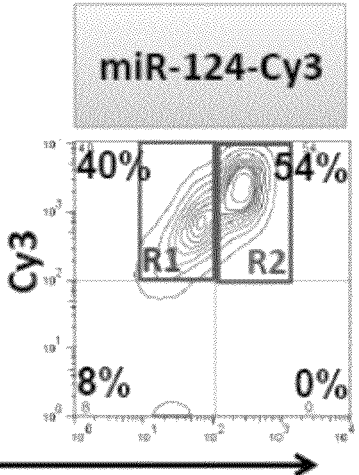

In most of these experiments, from 30 to 50% of macrophages down-regulated activation markers. It was theorized that this was due to incomplete transfection efficiency, however, the transfection experiments with Cy3-labeled control or miR-124 oligonucleotides (FIGS. 3h,i) demonstrated that at least 85% of macrophages incorporated the oligonucleotides. It has been reported that macrophages are difficult to transfect due to degradation of DNA or RNA in the lysosomal compartment[29]. Therefore, intracellular localization of fluorescent Cy3-labeled miR-124 was investigated using macrophages co-transfected with ORGANELLE LIGHTS™ (Invitrogen) that labels lysosomes with GFP tagged protein, and analyzed them by imaging cytometry (Aminis Inc.). miR-124$^+$CD45$^{hi}$ and miR-124$^+$CD45$^{low}$ cell populations (corresponding to R2 and R1 quadrants in FIG. 3i) were analyzed individually. Notably, in 78% of miR-124$^+$CD45$^{hi}$ cells Cy3-miR-124 was localized to lysosomes. On the contrary, in miR-124$^+$CD45$^{low}$ cells miR-124 was localized to cytoplasm. These data suggest that functional (i.e. cytosolic) overexpression of miR-124 causes deactivation of BM-derived macrophages by lowering expression of activation markers, inhibition of expression of TNFα, decrease in proliferation, and morphological changes. The cells in which miR-124 is targeted to the lysosomal compartment and undergo lysosomal degradation exhibited an unaffected activated phenotype.

Example 4

Overexpression of miR-124 in Macrophages Resulted in the Direct Down-Regulation of CEBPα and Downstream Effects on PU.1

Figure 4A:
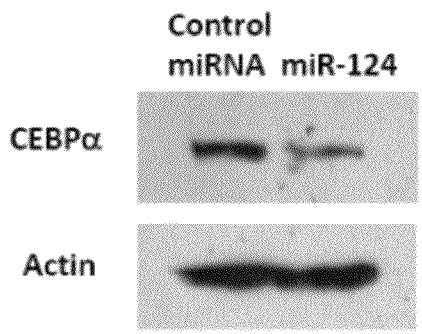
FIG. 4a shows an image of a Western blot of BM-derived macrophages transfected twice with miR-124 or control miRNA as for FIG. 3, and analyzed for CEBPα expression by Western blotting 48 hours after the second transfection.
Figure 4H:
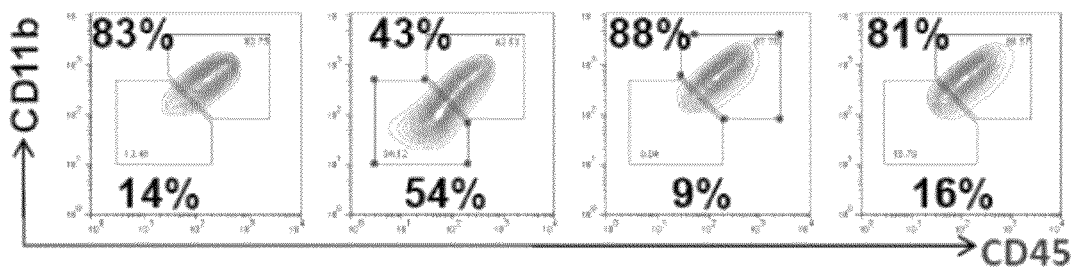
Figure 4I:
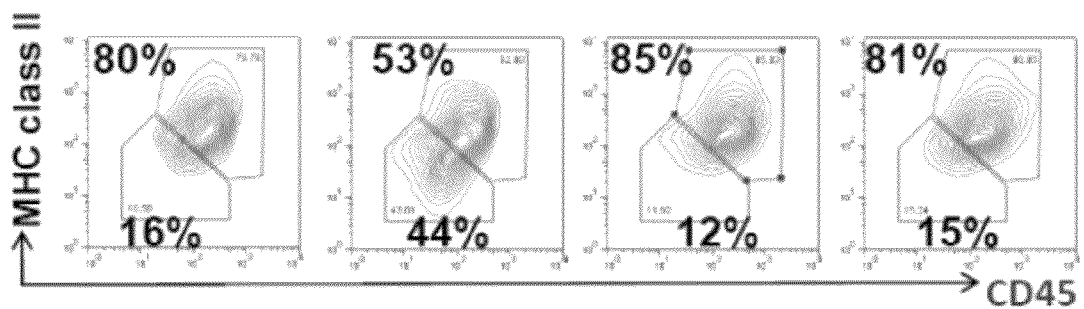
Figure 4J:
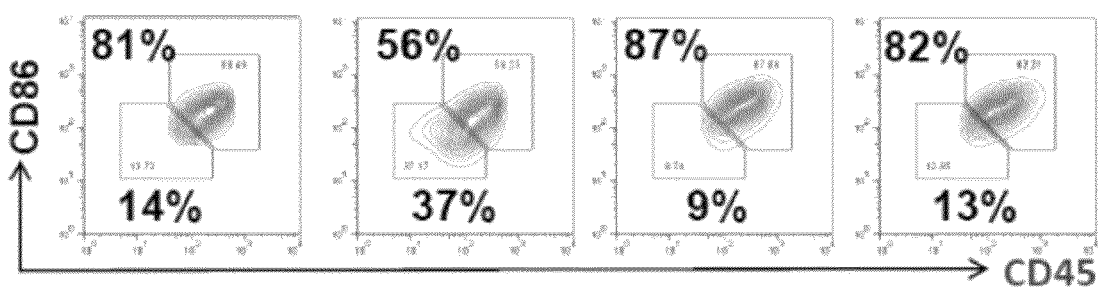

Since miR-124 deactivated macrophages (FIG. 3), the mechanism underlying this was investigated effect. Using the "TARGETSCAN™" algorithm[30], in silico analysis of mRNA targets predicted for miR-124 was performed. CEBPα a master transcription factor involved in differentiation of myeloid cells[31,32], was predicted as a putative target with three conserved miR-124 binding sites within its 3'-UTR (FIG. 4d). The CEBPα protein level was reduced 2-3-fold in miR-124-transfected BM-MΦ, as indicated by Western blotting (FIG. 4a). Two-color flow cytometry further confirmed that transfection of macrophages with miR-124 resulted in downregulation of both CD45 and CEBPα (FIG. 4b, CEBPα). Specifically, the population of CD45$^{hi}$CEBPα$^+$ cells decreased from 58% to 21% whereas the population of CD45$^{low}$CEBPα$^-$ cells increased from 19% to 58%. This indicates that the CEBPα negative phenotype corresponded to the CD45$^{low}$ phenotype of macrophages. Expression of the transcription factor PU.1, which is regulated by CEBα and also required for differentiation of monocytic lineage cells[32-34], was down-regulated by miR-124 as well (FIG. 4b, PU.1). Quantification of the four experiments demonstrates that mir-124 overexpression decreases the percentage of CD45CEBPα$^+$ and CD45$^{hi}$PU.1$^+$ cells 3-fold and 4-fold, respectively (FIG. 4c).

The next experiments sought to confirm that miR-124 directly binds and down-regulates the expression of CEBPα using a luciferase reporter system. Mouse neuroblastoma cell line NI-E115, which does not express CEBPα and exhibits a low level of endogenous miR-124 expression, was transfected with a construct containing full-length CEBPα 3'UTR sequence downstream of firefly luciferase (FIG. 4e). The transfected cells exhibited luciferase activity, which was inhibited 3.6-fold by co-transfection with miR-124 (FIG. 4e, CEBPA). Mutations of this reporter construct within two predicted miR-124 binding sites (FIG. 4d, sites 1-2) significantly reduced the luciferase responsiveness to miR-124 (FIG. 4e, CEBPAmut1-2). When all three predicted miR-124 binding sites in the 3'-UTR of CEBPα were mutated (FIG. 4d, sites 1-3), the construct responsiveness to miR-124 was abolished (FIG. 4e, CEBPAmut1-3). These data validate the regulatory potential of miR-124 mediated by the three binding sites and confirmed CEBPα as its direct target gene.

These experiments demonstrated that miR-124 overexpression causes down-regulation of transcription factor PU.1 (FIG. 4b, PU.1) and activation markers CD45, MHC class II, and CD86 (FIG. 3a,b). According to the target prediction analysis in silico, miR-124 regulates neither PU.1 mRNA nor mRNAs for activation markers CD45, CD11b, F4/80, MHC class II, and CD86 directly. Since CEBPα binds to the promoter region of PU.1 and induces its transcription[33,34], it was hypothesized that miR-124 down-regulates PU.1 indirectly through the inhibition of CEBPα. To test this hypothesis, mice with conditional knockout of the cebpa gene were used.

BM was isolated from WT or CEBPA$^{F/F}$ mice and BM-MΦ were expanded in vitro. Poly I:C that induces expression of Mx1-Cre (and thus resulted in knockout of the cebpa gene) was added to cultures derived from CEBPA$^{F/F}$ but not from WT mice (FIGS. 4$f$-$j$). Conditional knockout of the cebpa gene caused a reduction in levels of CEBPα protein (FIG. 4$f$, CEBPA$^{Δ/Δ}$), which resulted in reduced expression of PU.1 (FIG. 4$g$, CEBPA$^{Δ/Δ}$), CD11b (FIG. 4$h$, CEBPA$^{Δ/Δ}$), MHC class II (FIG. 4$i$, CEBPA$^{Δ/Δ}$), and CD86 (FIG. 4$j$, CEBPA$^{Δ/Δ}$). The extent of down-regulation of CEBPα and PU.1 in CEBPA$^{Δ/Δ}$ macrophages (FIGS. 4$f$-$g$, CEBPA$^{Δ/Δ}$) was comparable to that observed in WT macrophages after miR-124 overexpression (FIGS. 4$f$-$g$, miR-124).

These data suggest that miR-124 controls multiple markers of macrophage activation by direct inhibition of CEBPα and its downstream transcription factor PU.1.

Example 5

Peripheral Administration of miR-124 Resulted in Inhibition of EAE and Reduction of CNS Inflammation Since miR-124 expression regulated macrophage activation, whether systemic administration of miR-124 in vivo affects the course of EAE was investigated. Administration of miR-124 during the preclinical stage of EAE (beginning on day seven after disease induction) completely prevented disease symptoms (FIG. 5$a$). Treatment of mice with miR-124 at the onset of EAE (starting day 13 after EAE induction) also substantially ameliorated clinical symptoms and enhanced recovery (FIG. 5$b$). These studies were carried out in B6 mice. It was then investigated whether miR-124 suppressed EAE in other strains including those with more severe forms of the disease. Disease symptoms were also substantially ameliorated in both EAE-prone SJL mice (FIG. 5$f$) as well as in IFNγ$^{-/-}$ mice (FIG. 5$g$) that have a more severe form of EAE.

To assess changes in inflammatory responses in mice with EAE treated with miR-124, groups of 4-5 mice were sacrificed at day 21 (when the control group had peak EAE), and mononuclear cells were isolated from CNS and spleens. CD11b$^-$CD45$^{hi}$ peripheral macrophages/activated microglia (FIG. 5$c$, Control miRNA, region R2) and CD11b$^-$CD45$^{hi}$ leukocytes (FIG. 5$c$, Control miRNA, region R3) were detected in the CNS of mice from the control group. In contrast, the mice treated with miR-124 had primarily CD11b$^+$CD45$^{low}$ resting microglia (FIG. 5$c$, miR-124, region R1) and no signs of microglia activation or leukocyte infiltration in the CNS (FIG. 5$c$, miR-124, regions R2 and R3). This suggests that peripheral administration of miR-124 suppressed EAE symptoms and leukocyte infiltration in the CNS (Table 2). The decrease in absolute number of CNS macrophages/activated CD45$^{hi}$ microglia, lymphocytes and CD4 T cells after treatment with miR-124 is shown in FIG. 5$d$. Histologic analysis was performed, and inflammatory lesions containing nucleated and CD11b$^-$ cells in the white matter of the lumbar spinal cord were evident in the control group (FIG. 5$e$, upper images) but undetectable in the miR-124 treated mice (FIG. 5$e$, lower images). Thus treatment of mice with miR-124 resulted in both amelioration of EAE symptoms and inflammation in the CNS.

TABLE 2

Analysis of mononuclear cells isolated from the CNS of mice with EAE treated with miR-124 or control miRNA[1].

| | Microglia Region R1 (CD11b$_+$ CD45$_{low}$) | Activated microglia and peripheral macrophages Region R2 (CD11b$_+$CD45$_{hi}$) | Lymphocytes Region R3 (CD11b$_-$ CD45$_{hi}$) | CD4 T cells (CD3$_+$CD4$_+$) |
|---|---|---|---|---|
| Control miRNA | 68 ± 6 | 12 ± 3 | 18 ± 4 | 11 ± 2 |
| miR-124 | 93 ± 2[2] | 3 ± 1[3] | 2 ± 1[4] | 1.6 ± 0.4[4] |

Figure 5A:
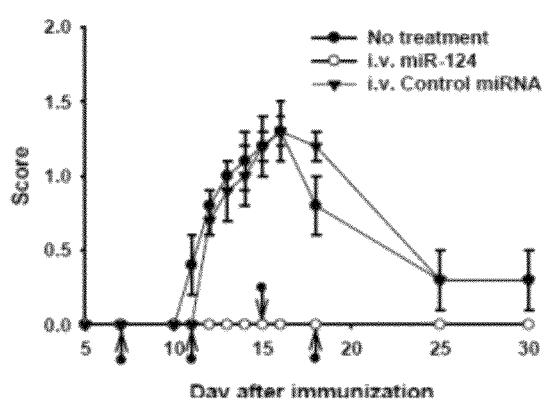
FIGS. 5a-b are line graphs showing the EAE disease course in mice treated with miR-124. Mice with EAE were injected i.v. with miR-124 or control miRNA on days 7, 11, 15, and 18 (5a) or days 13, 16, 18, 20, and 22 (5b) after EAE induction as indicated by arrows. The data represents the average of three experiments with 4-5 mice per group.
Figure 5B:
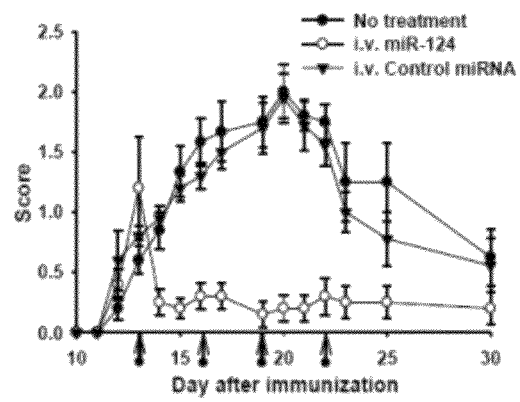
Figure 5C:
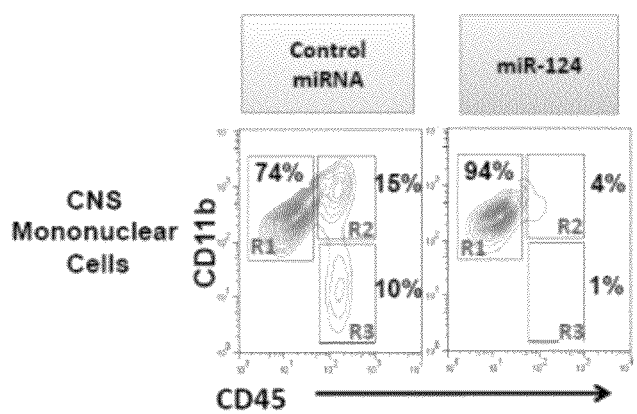
FIG. 5c shows the results of flow cytometry analysis of CNS infiltrating cells isolated from mice treated with miR-124 vs. control miRNA. Mice with EAE were injected i.v. with miR-124 or control miRNA on days 13, 16, 18, and 20 after EAE induction as for (5b) and mononuclear cells were isolated from CNS on day 21, stained for CD11b and CD45 and analyzed by flow cytometry Staining for CD11b (y-axis) and CD45 (x-axis) of CNS mononuclear cells is shown. Percentages of populations of resting CD11b$^+$CD45$^{low}$ microglia (Region R1), CD11b$^+$CD45$^{hi}$ activated microglia and peripheral macrophages (Region R2) and CD11b$^-$CD45$^{hi}$ lymphocytes (Region R3) are shown.
Figure 5D:
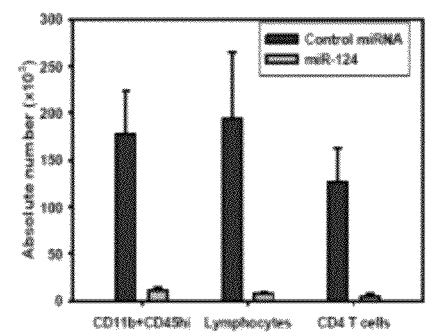
FIG. 5d is a bar graph showing the quantification of absolute number of activated microglia/macrophages, lymphocytes and CD4 T cells in the CNS of mice treated with either miR-124 or control miRNA. The absolute numbers of CD11b$^+$CD45$^{hi}$ activated microglia/peripheral macrophages and CD11b$^-$CD45$^{hi}$ lymphocytes were calculated by multiplying the total cell count obtained using hemocytometer by the percentage of these cells determined by flow cytometry as in (5c) and then dividing by the number of mice in each group. The absolute number of CD4 T cells was determined by staining CNS mononuclear cells for CD4 and CD3 and using percentage of CD3$^+$CD4$^+$ cells. Mean±S.E. of three independent experiments is shown.
Figure 5E:
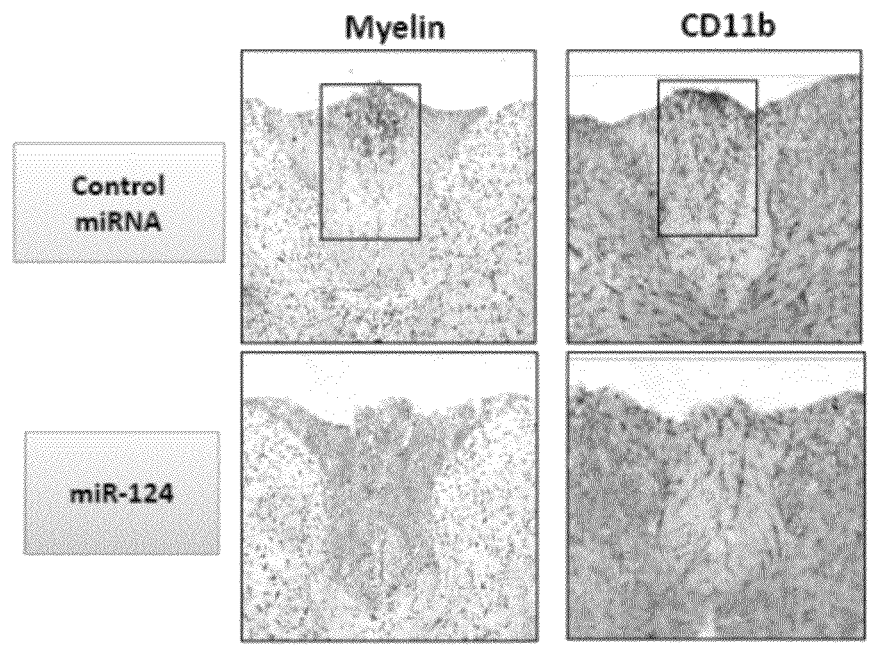
FIG. 5e is a photomicrograph of spinal tissue from mice treated with control miRNAs or miR-124 as for (5b). Spinal cords were harvested on day 21 following induction of EAE. Frozen 10-μm coronal sections of spinal cord were stained for Myelin (Luxol Fast Blue) or CD11b. Each individual panel shows a representative histopathology image (×200); three mice were analyzed. Myelin sheath is shown as medium gray and nucleated cells are dark gray (left panels). The cells colored dark grey are positive for CD11b (right panels).
Figure 5F:
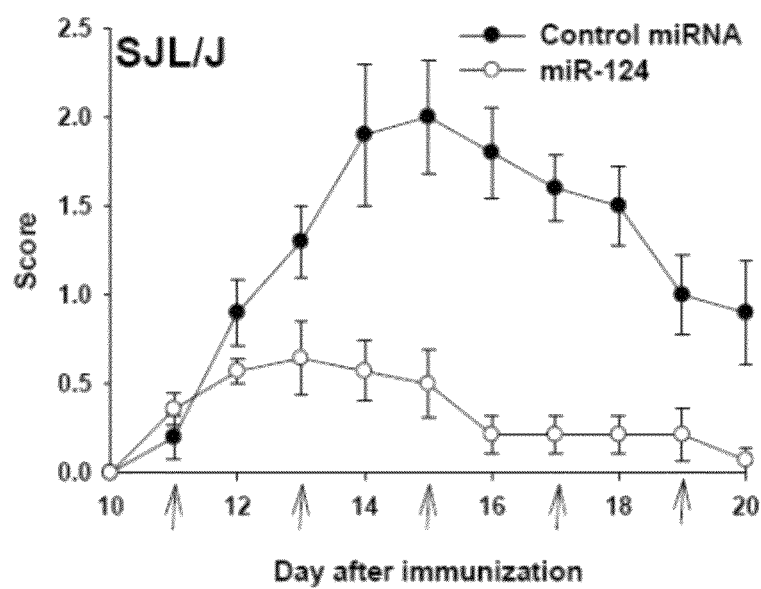
FIGS. 5f-g are line graphs showing that peripheral administration of miR-124 suppresses EAE clinical symptoms in SJL and IFNgamma$^{-/-}$ mice. In 5f, EAE was induced in SJL mice by immunization with PLP139-151 in CFA. Mice with EAE were injected i.v. with miR-124 or control miRNA on days 11, 13, 15, 17 and 19 after EAE induction as indicated by arrows. EAE clinical score was evaluated daily. The data represent an average of three experiments with 3-5 mice per group. In 5g, EAE was induced in IFNgamma$^{-/-}$ mice by immunization with MOG as for FIG. 5a,b. Mice with EAE were injected i.v. with miR-124 or control miRNA on days 13, 15, 17, 19, 21, 23, 25, 27 and 29 after EAE induction as indicated by arrows. EAE clinical score was evaluated daily. The data represent an average of three experiments with 3-5 mice per group.
Figure 5G:
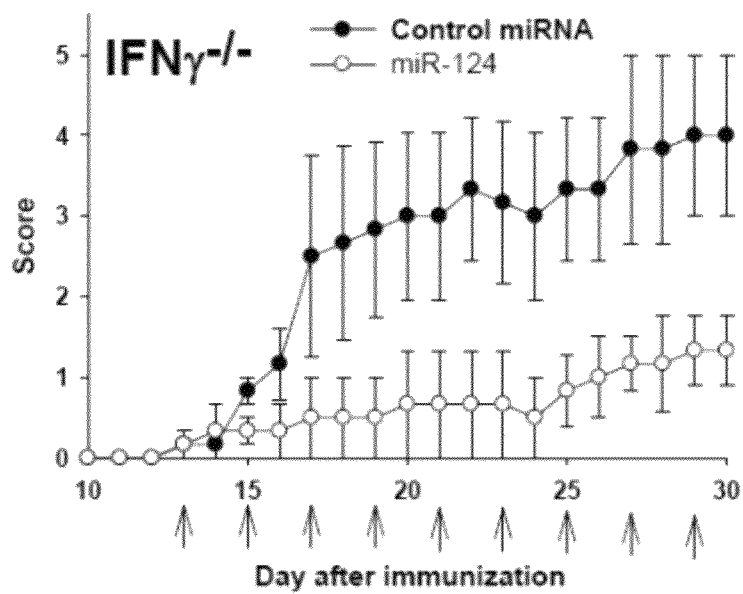
Figure 5H:
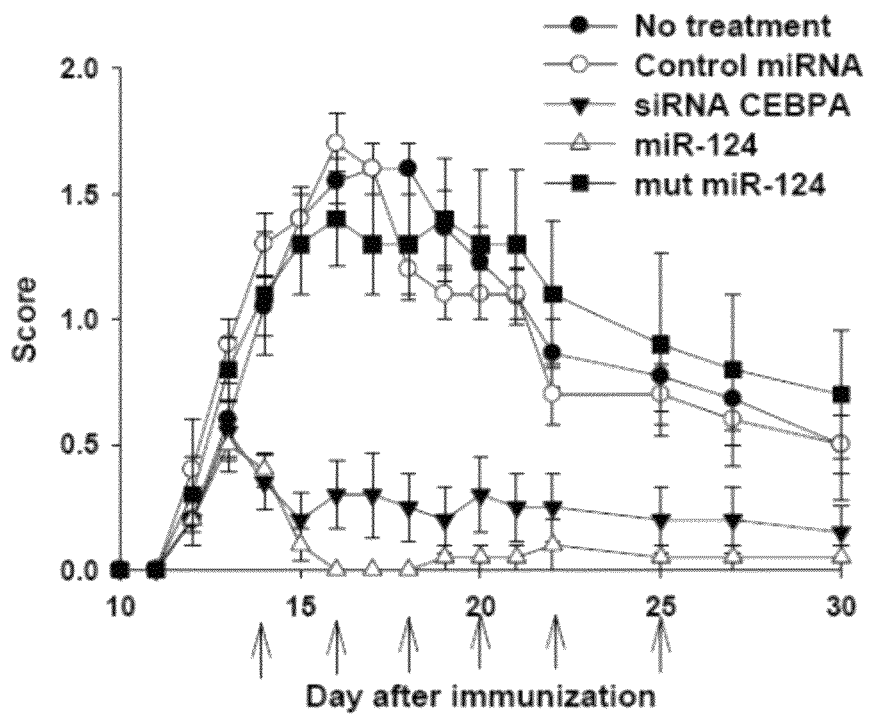
FIGS. 5h-i are line graphs showing that knockdown and conditional knock out of CEBPa results in EAE suppression similar to that observed with miR-124 treatment. In 5h, EAE was induced in B6 mice as for FIG. 5a,b. Mice with EAE were injected i.v. either with siRNA for CEBPA, miR-124, control miRNA, or mutant miR-124 on days 14, 16, 18, 20, 22 and 25 after EAE induction as indicated by arrows. The data represent an average of three experiments with 4-5 mice per group. In 5i, EAE was induced in CEBPAF/F or B6 mice as for FIG. 6. Poly I:C (100 ug per mouse) was injected i.p. at indicated by arrows time points to induce expression of Mx1-Cre and delete the cebpa gene. The data represent an average of three experiments with 4-5 mice per group.
Figure 5I:
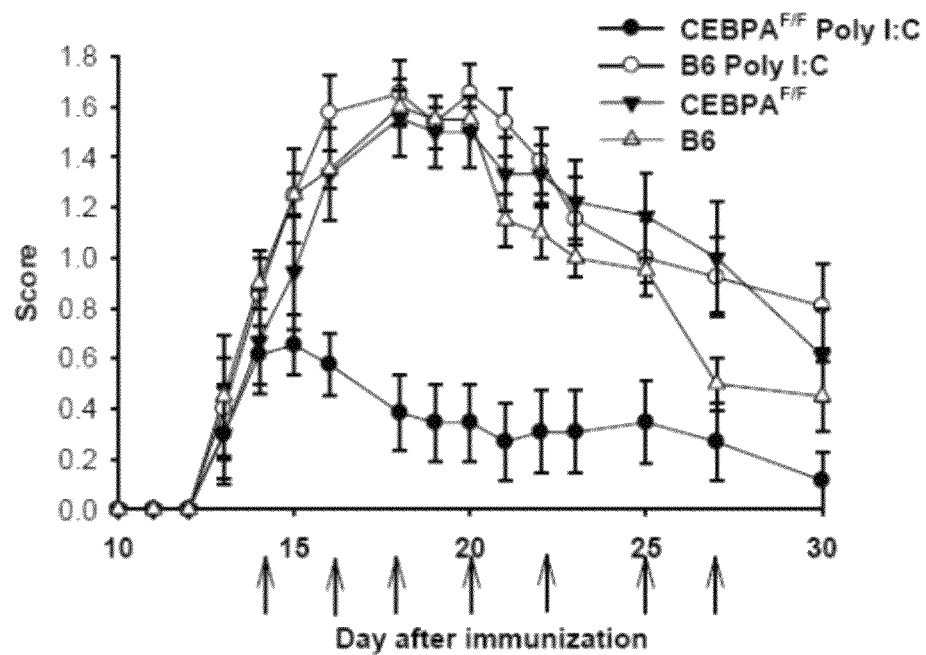
Figure 6A:
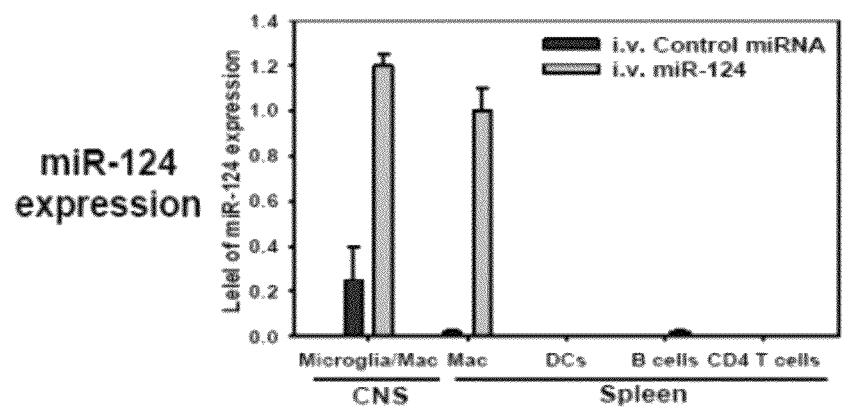
FIG. 6a is a bar graph showing that peripheral administration of liposomes with miR-124 resulted in up-regulation of miR-124 in macrophages, but not in dendritic cells, B Cells or CD4 T Cells. Mice with EAE were injected i.v. with miR-124 or control miRNA on days 13, 16, 18, and 20 after EAE induction as described in Methods. On day 21 the mice were sacrificed, brain/spinal cords and spleens of 4-5 mice pooled, and populations of CNS CD11b$^+$F4/80$^+$ microglia/macrophages and splenic CD11b$^+$F4/80$^+$ macrophages, CD11c$^+$CD205$^+$ dendritic cells, CD 19$^+$B220$^+$B cells, and CD4$^+$CD3$^+$CD4 T cells sorted and examined for miR-124 expression by real-time RT-PCR.
Figure 6B:
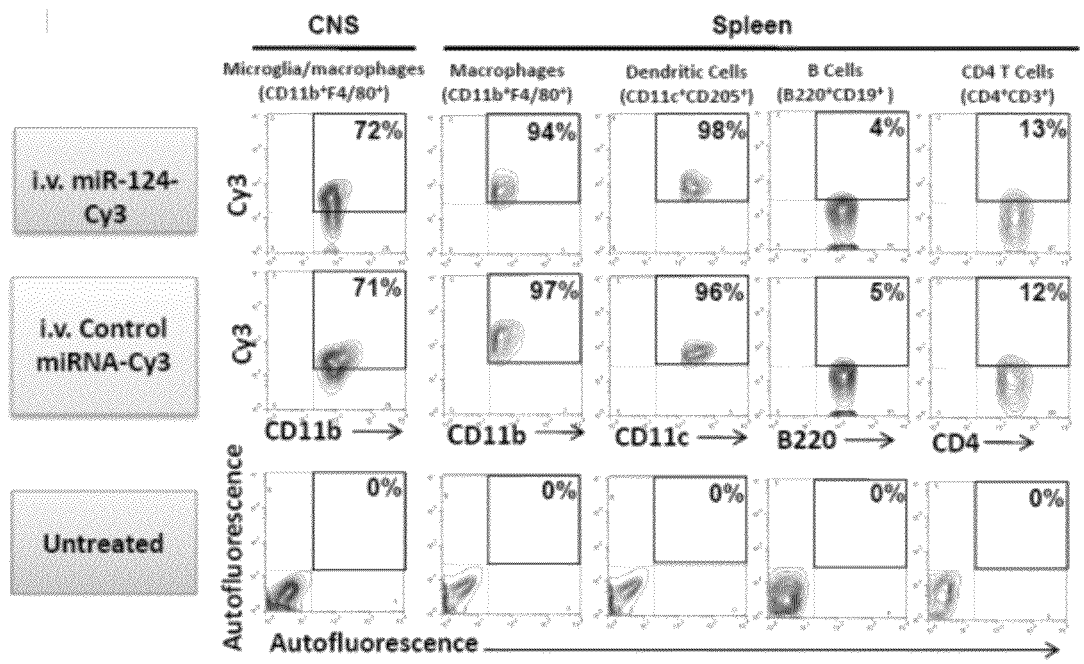
FIGS. 6b-c show the results of experiments in which mice with EAE were injected i.v. with Cy3-labeled miR-124 or Cy3-labeled control miRNA on days 13, 16, 18, and 20 after EAE induction. On day 21 the mice were sacrificed, mononuclear cells isolated from CNS and spleen, stained for surface markers, and the populations of CD11b$^+$F4/80$^+$ gated macrophages, CD11c$^+$CD205$^+$ dendritic cells, CD19$^+$B220$^+$B cells, and CD4$^+$CD3$^+$CD4 T cells were analyzed for Cy3 fluorescence by three-color flow cytometry. 15 FACS plots from a representative experiment are shown in 6b, and the mean±S.E. of individual mice from three separate experiments is shown in bar graph form in 6c.
Figure 6C:
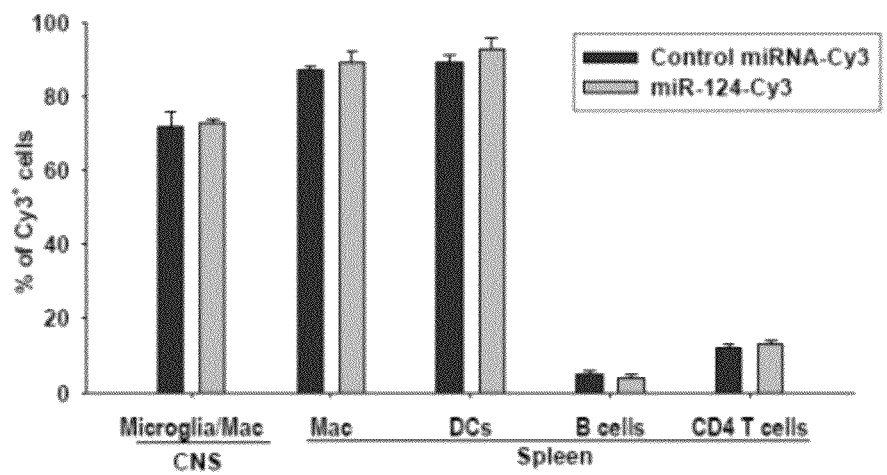
Figure 6D:
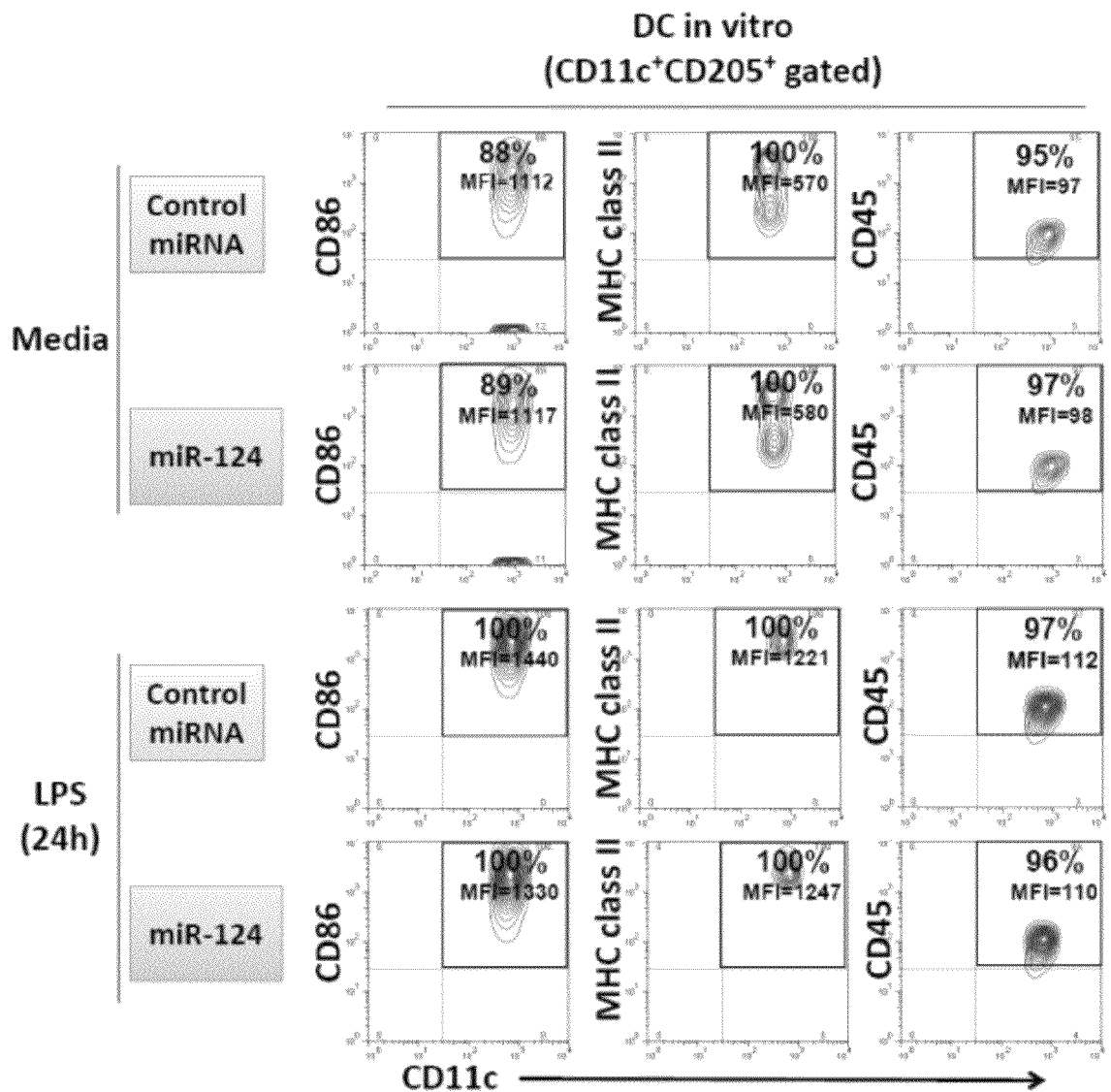
FIG. 6d is a set of 12 FACS plots showing that in vitro transfection of dendritic cells with miR-124 does not affect phenotype of dendritic cells BM-derived dendritic cells were expanded in GM-CSF as described in Methods, and transfected twice with miR-124 as for macrophages in FIG. 3. 48 hours after the second transfection the cells were stained for CD11c, CD205, CD86, MHC class II and CD45. Expression of CD11c (x-axis) and CD86, or MHC class II, or CD45 (y-axis) for CD11c+CD205+ gated cells is shown. To promote maturation of dendritic cells, LPS (100 ng/ml) was added to some cultures 24 hours prior to the analysis (labeled as "LPS") as described in Methods, other cultures were incubated without LPS (labeled as "Media").

[1] Mice with EAE were injected with miR-124 or control miRNA as in FIG. 5b, and on day 21 after EAE induction mononuclear cells were isolated and analyzed for the expression of surface markers and intracellular CEBP. Mean percentages of indicated populations ± S.E. of three individual experiments are shown.
[2] $p < 0.01$ compared to control miRNA.
[3] $p < 0.05$ compared to control miRNA.
[4] $p < 0.005$ compared to control miRNA.
[5] $p < 0.0001$ compared to control miRNA.

Next, whether amelioration of EAE symptoms was due to the reduced level of CEBPα expression was assessed. i.v. injected siRNA specific for CEBPα had similar effects on disease symptoms, whereas mutant miR-124 lacking CEBPα mRNA binding sequence had no effect on the disease score (FIG. 5$h$). Finally, conditional knock out of cebpa gene also resulted in amelioration of EAE (FIG. 5$i$).

Example 7

Peripheral Administration of miR-124 During EAE has a Direct Effect on Macrophages, but not on Dendritic Cells, CD4 T Cells or B Cells The mechanisms by which miR-124 affected EAE were investigated by examining which immune cells incorporated miR-124.

Repeated i.v. injection of liposomes with miR-124 into mice with EAE resulted in increased miR-124 expression in the CNS microglia/macrophages, and in the population of splenic macrophages (which do not express endogenous miR-124), but not in splenic dendritic cells (DCs), CD4 T cells or B cells, as detected by quantitative real-time RT-PCR (FIG. 6$a$). Using fluorescently labeled miR-124 or control miRNA, 72-73% of microglia/macrophages in the CNS became fluorescent after peripheral administration of these molecules during EAE. In the spleen 87-89% of macrophages became fluorescent, whereas less than 4-5% of B cells and 12-13% of CD4 T cells were positive for Cy3 labeled miR-124 or control miRNA (FIGS. 6$b$,$c$). These data further confirmed that systemically administered miR-124 is primarily delivered to macrophages, but not to B cells or CD4 T cells (FIG. 6$a$-$c$). Interestingly, 89-93% of dendritic cells incorporated fluorescent miR-124 or control miRNA as detected by FACS (FIG. 6$b$-$c$). Nevertheless, miR-124 expression was not detected in these cells by quantitative real-time PCR (FIG. 6$a$), suggesting that the miRNA was quickly degraded and thus not functional. To further investigate whether miR-124 had a functional role in dendritic cells, miR-124 was transfected into BM-derived DCs grown in vitro in the presence of GM-CSF. These transfections had no effect on immature and LPS-matured DCs, as monitored by the expression of CD45, MHC class II and CD86 (FIG. 6$d$). Thus, these data suggest that peripheral administration of miR-124 during EAE results in miR-124 overexpression in macrophages, but not in DCs, B cells or CD4 T cells.

Example 8

Peripheral Administration of miR-124 Deactivates Macrophages and Inhibits the Activation of Autoimmune CD4 T Cells In Vivo The mechanism by which miR-124 affected EAE was further investigated by examining effect of miR-124 on macrophages and CD4 T cells.

Figure 7O:
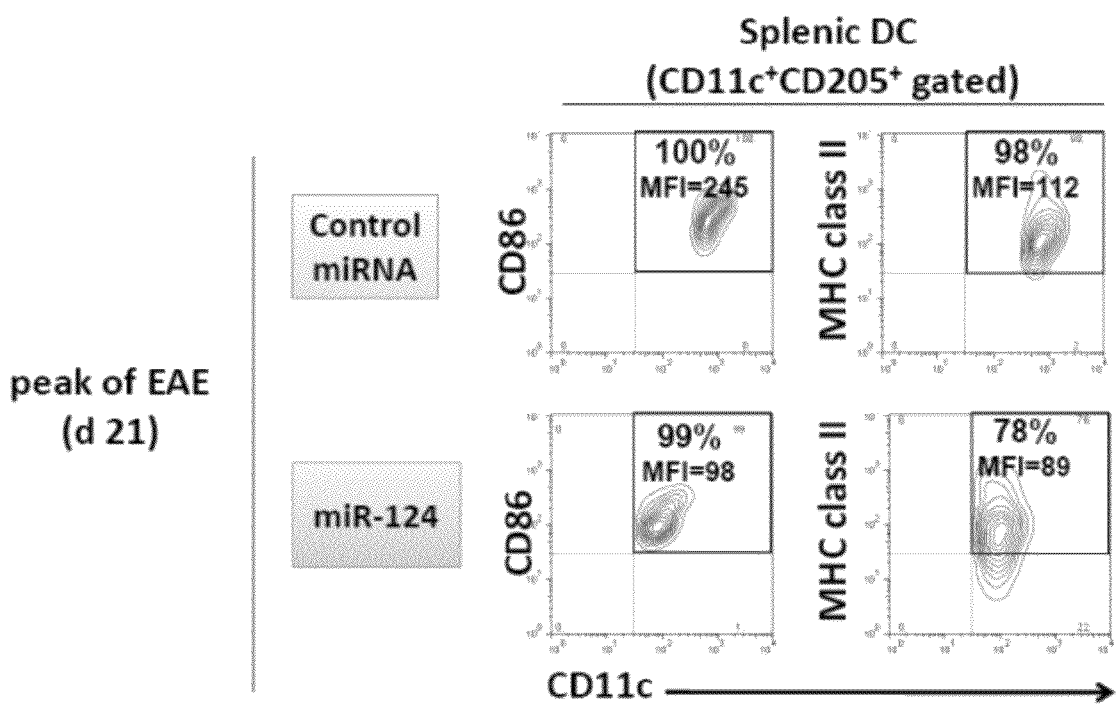
FIG. 7o is a set of four FACS plots showing that peripheral administration of miR-124 decreases expression of MHC class II and CD86 on splenic dendritic cells. Mice with EAE were injected i.v. with miR-124 or control miRNA on days 13, 16, 18, and 20 as for FIG. 5b. Mononuclear cells were isolated from spleens on day 21 after EAE induction, stained for expression of CD11c, CD205, MHC class II and CD86, and analyzed by three-color flow cytometry. Staining for CD11c (x-axis), and CD86 or MHC class II (y-axis) of CD11c+CD205+ gated cells is shown. Percentage and mean fluorescent intensity (MFI) for MHC class II and CD86 is shown in upper right quadrants.

After treatment with miR-124 splenic macrophages exhibited a $CD45^{int/low}$MHC class $II^-$ phenotype (FIG. 7b) that resembled that of resting microglia (FIG. 7a), suggesting that miR-124 deactivated macrophages in the periphery. Further analysis of CEBPα, a miR-124 target gene, revealed that CEBPα was down-regulated in both CNS and spleen (FIGS. 7c,d). The $CD45^{low}$ population of macrophages in the spleen was virtually negative for CEBPα (FIG. 7d), which is consistent with the previous findings in vitro (FIG. 4b). Data from three independent experiments are summarized in Table 3. Systemic injection of miR-124 also resulted in the reduced production of the pro-inflammatory cytokines TNFα and IL-6 in both CNS and spleen (FIG. 7e-h, Table 3), which is consistent with the decreased production of TNFα following miR-124 transfections of macrophages in vitro (FIG. 3c). The treatment of mice with miR-124 also lowered expression of MHC class II and CD86 on dendritic cells in vivo (FIG. 7o). Since there are no direct effects of miR-124 on dendritic cells in vitro (FIGS. 5f-g), miR-124 administration may affect dendritic cells in vivo indirectly by lowering TNFα, a cytokine critical for development/maturation of dendritic cells[35] production by macrophages (FIG. 7e-f). Thus, peripheral administration of miR-124 resulted in the direct deactivation of macrophages and indirect deactivation of DCs.

The deactivation of macrophages and dendritic cells that was observed could in turn impair their ability to present antigen to autoimmune T cells. Indeed, in both CNS and spleen of mice with EAE treated with miR-124, CD4 T cells had reduced expression of activation markers such as CD69 (FIG. 7i-j, Table 3), substantially lower production of the proinflammatory cytokine IFNγ (FIG. 7k-l, Table 3) and decreased proliferation as determined by BrdU incorporation (FIG. 7m-n, Table 3).

The decreased ability of macrophages and dendritic cells to present antigen could result in deficient priming of autoimmune cells. To investigate whether miR-124 influenced priming of myelin-specific T cells in vivo, MOG-TCR transgenic 2D2 mice were immunized with $MOG_{35-55}$ peptide and injected them i.v. with either miR-124 liposomes or control miRNA every other day for one week.

Administration of miR-124 downregulated the activation markers CD69, CD25 and CD44 on CD4 T cells, upregulated the naïve T cell marker CD69L and reduced by two-fold the percent of BrdU-positive $CD4^+$ gated cells in a subsequent in vitro recall response (FIG. 7p), demonstrating a decrease in activation of MOG-specific T cells. Thus, peripheral administration of miR-124 causes deactivation of macrophages accompanied by a decrease in proliferation of autoimmune T cells and suppression of EAE.

Example 9

The Effect of miR-124 Inhibitors on the Phenotype of Microglia and Macrophages To further investigate the hypothesis that expression of miR-124 is required for microglia to maintain the quiescent $CD45^{low}$ MHC class $II^{low}$ phenotype in normal CNS, miR-124 knockdown experiments were performed in vivo and in vitro. To knockdown miR-124 in vivo, miR-124 antisense oligonucleotide inhibitor (anti-miR-124) was injected intracranially. Injection of fluorescently labeled ani-miR-124 resulted in incorporation of this inhibitor into 20-30% of $CD11b^+$ gated cells (FIG. 8a). When injected into B6→$CX3CR1^{GFP/+}$ chimeric mice that express GFP in microglia but not in peripheral macrophages, anti-miR-124 induced the activation of $CD11b^-GFP^+$ microglia as measured by up-regulation of MHC class II and CD45 (FIGS. 8b,c). In addition, in vivo administration of anti-miR-124 altered the morphology of microglia. $GFP^+$ microglia in chimeric mice injected with anti-miR-124 resembled macrophages, with an increase in size and a loss of the processes network as quantified in FIG. 8d.

The effects of knocking down miR-124 in vitro were then investigated. To knockdown miR-124 in vitro ex-vivo isolated adult microglia or long-term cultures of these cells was

TABLE 3

Analysis of activation markers and cytokine expression in populations of CD4 T cells and CD11b+F4/80+ cells isolated from the CNS and spleens of mice with EAE treated with miR-124 or control miRNA[1]

| | | CD4 T cells | | | CD11b+F4/80+ gated | | | |
|---|---|---|---|---|---|---|---|---|
| | | CD69 | IFNγ | BrdU | MHC class II | CEBPα | TNFα | IL-6 |
| CNS | Control miRNA | 69 ± 3 | 42 ± 3 | 20 ± 3 | 58 ± 6 | 75 ± 4 | 34 ± 2 | 29 ± 2 |
| | miR-124 | 41 ± 6[2] | 11 ± 3[3] | 8 ± 2[2] | 3 ± 2[4] | 53 ± 6[2] | 8 ± 2[4] | 9 ± 2[4] |
| Spleen | Control miRNA | 85 ± 5 | 27 ± 8 | 18 ± 2 | 50 ± 3 | 68 ± 5 | 25 ± 5 | 72 ± 6 |
| | miR-124 | 55 ± 7[2] | 11 ± 2[2] | 8 ± 1[3] | 10 ± 1[4] | 23 ± 7[3] | 7 ± 2[3] | 55 ± 7 |

Figure 9A:
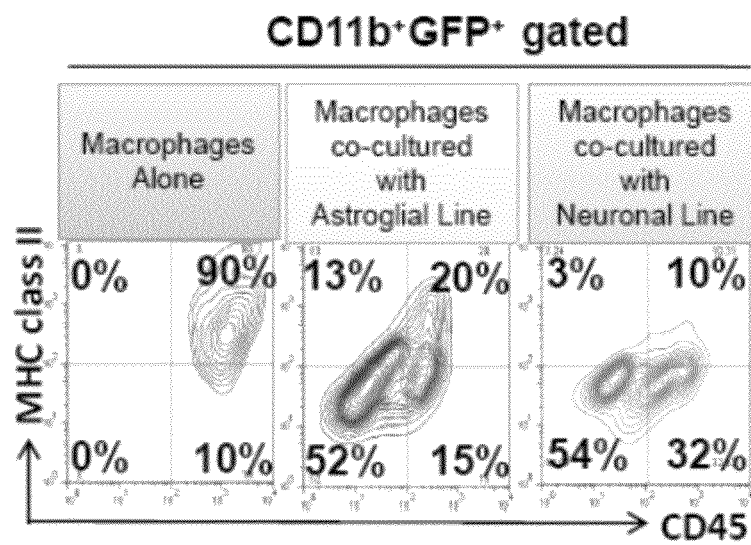
Figure 9B:
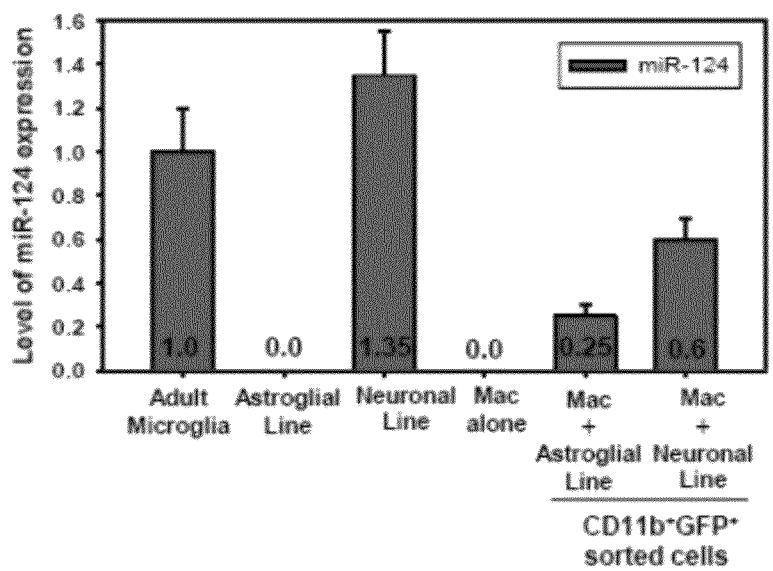

[1]Mice with EAE were injected with miR-124 or Control miRNA as in FIG. 5b, and on day 21 after EAE induction mononuclear cells were isolated and analyzed for the expression of surface markers and intracellular CEBPα. Mean percentages of populations positive for indicated markers or cytokine ± S.E. of three individual experiments are shown.
[2]$P < 0.05$ compared to control miRNA.
[3]$P < 0.01$ compared to control miRNA.
[4]$P < 0.001$ compared to control miRNA.

attempted[36]. Approximately 90% of isolated adult microglia survive for 6-12 hours ex-vivo, but not longer than 48 hours in culture, and the remaining cells do not express miR-124. This makes ex-vivo cultures not suitable for studying relatively long-term effects of the miRNA inhibitors. A different approach was then chosen. It was hypothesized that microglia/macrophages up-regulate miR-124 under the influence of the CNS microenvironment by receiving specific signals from CNS stromal cells such as astrocytes and neurons. To test this hypothesis, GFP⁺BM-MΦ (obtained from ACTB-GFP transgenic mice that ubiquitously express GFP under the actin promoter) were co-cultured with either an astroglial or neuronal cell line. After six days of the co-culture, the macrophages acquired a deactivated microglia-like phenotype as indicated by down-regulation of both CD45 and MHC class II (FIG. 9a). Furthermore, the acquisition of the microglial phenotype was accompanied by the up-regulation of miR-124 in CD11b⁺GFP⁺ sorted macrophages (FIG. 9b).

This co-culture system allowed us to investigate whether transfection of the anti-miR-124 affected the expression of MHC class II and CD45 in macrophages. As shown in FIGS. 9c,d, the treatment with the inhibitor of miR-124 attenuated the down-regulation of MHC class II and CD45. It also inhibited the development of the ramified microglia-like morphology in GFP⁺ macrophages co-cultured with astroglial and neuronal lines (not shown). The effect of the miR-124 inhibitor on the percentage of CD45$^{hi}$MHC class II⁺ macrophages co-cultured with astroglial and neuronal lines is summarized in FIG. 9e. These data demonstrate that miR-124 plays a role in maintaining the quiescent phenotype of microglia in normal CNS as driven by their paracrine interaction with local stromal cells.

Example 10

Effect of miR-124 Administration in an Animal Model of ALS

The effect of miR-124 treatment on clinical symptoms was assessed in the SOD1 (G93A) mouse model of ALS.

Figure 10:
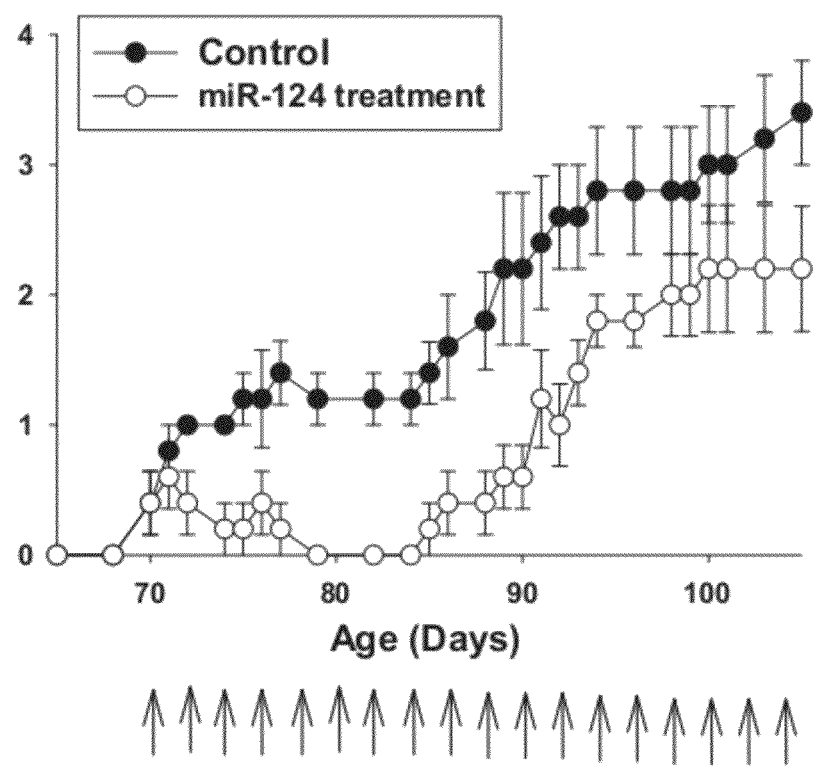
FIG. 10 is a line graph showing the effect of miR-124 treatment on clinical symptoms was assessed in the SOD1 (G93A) mouse model of ALS. 30 ug of miR-124 was injected at time points indicated by arrows, starting from disease onset, and clinical symptoms were assessed as follows: 0, no symptoms; 1, movement abnormalities; 2, hind limp paresis/paralysis; 3, hind and fore limb paralysis; 4, death or euthanasia. Data are presented as mean±S.E. of five mice per group.

Briefly, 30 ug of miR-124 in LIPOFECTAMINE2000 was injected i.v. (200 ul/mouse) at time points indicated by arrows in FIG. 10, starting from disease onset, and clinical symptoms were assessed as follows: 0, no symptoms; 1, movement abnormalities; 2, hind limp paresis/paralysis; 3, hind and fore limb paralysis; 4, death or euthanasia. Data are presented as mean±S.E. of five mice per group.

These results indicate that treatment with mR-124 may have therapeutic benefit in autoimmune diseases such as ALS.

Other Embodiments

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

Thus it is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating multiple sclerosis in a subject in need thereof, the method comprising administering to the subject a therapeutically effective amount of micro RNA-124 (miR-124) comprising the sequence UAAGGCACGCG-GUGAAUGCC (SEQ ID NO:1).

2. The method of claim 1, wherein the multiple sclerosis is characterized by activation of macrophages.

3. The method of claim 1, wherein the miR-124 is formulated for systemic administration.

4. The method of claim 1, wherein the miR-124 is modified.

5. The method of claim 1, wherein the miR-124 is modified to include a cholesterol group, 2'-O-methyl group, a 2'-fluoro group, a 2'-O-methyoxyethyl group, a phosphorothiate group, a boranophosphate group, or a 4'-thioribose group.

* * * * *

UNITED STATES PATENT AND TRADEMARK OFFICE
CERTIFICATE OF CORRECTION

PATENT NO. : 8,962,583 B2  
APPLICATION NO. : 13/379374  
DATED : February 24, 2015  
INVENTOR(S) : Howard Weiner et al.

Page 1 of 1

It is certified that error appears in the above-identified patent and that said Letters Patent is hereby corrected as shown below:

On the title page, column 2 (Other Publications), line 18, delete "Boillee" and insert -- Boullee --;

In the Specification
In column 1, line 9, delete "20102009," and insert -- 2009 --;

In the Claims
In column 45, line 15, in claim 5, delete "2'-O-methyoxyethyl" and insert -- 2'-O-methyloxyethyl --;
In column 45, line 15, in claim 5, delete "phosphorothiate" and insert -- phosphorothioate --.

Signed and Sealed this
Twenty-first Day of July, 2015

Michelle K. Lee
*Director of the United States Patent and Trademark Office*